United States Patent
Otvos et al.

(10) Patent No.: US 11,231,429 B2
(45) Date of Patent: *Jan. 25, 2022

(54) CARDIOVASCULAR RISK EVALUATIONS USING A RISK PARAMETER THAT INCLUDES AN HDL AND INFLAMMATORY BIOMARKER INTERACTION PARAMETER

(71) Applicant: LipoScience, Inc., Morrisville, NC (US)

(72) Inventors: James D. Otvos, Apex, NC (US); Irina Y. Shalaurova, Cary, NC (US)

(73) Assignee: Liposcience, Inc., Morrisville, NC (US)

(*) Notice: Subject to any disclaimer, the term of this patent is extended or adjusted under 35 U.S.C. 154(b) by 779 days.

This patent is subject to a terminal disclaimer.

(21) Appl. No.: 15/915,905

(22) Filed: Mar. 8, 2018

(65) Prior Publication Data

US 2018/0196075 A1 Jul. 12, 2018

Related U.S. Application Data

(63) Continuation of application No. 14/852,192, filed on Sep. 11, 2015, now Pat. No. 9,952,232.
(Continued)

(51) Int. Cl.
*G01N 33/48* (2006.01)
*G01N 33/50* (2006.01)
(Continued)

(52) U.S. Cl.
CPC .......... *G01N 33/92* (2013.01); *A61B 5/7275* (2013.01); *G01R 33/465* (2013.01);
(Continued)

(58) Field of Classification Search
CPC .............. G01N 33/92; G01N 2570/00; G01N 2800/32; G01R 33/465; A61B 5/7275; G16H 50/30
See application file for complete search history.

(56) References Cited

U.S. PATENT DOCUMENTS 9,952,232 B2 * 4/2018 Otvos ................. G01R 33/465
2003/0235918 A1 12/2003 Shewmake et al.
(Continued)

FOREIGN PATENT DOCUMENTS

CN 101371144 2/2009
CN 101512384 8/2009
(Continued)

OTHER PUBLICATIONS

Jeyarajah, E. et al., Lipoprotein particle analysis by nuclear magnetic resonance spectroscopy, Clin Lab Med, 2006, vol. 26, pp. 847-870.
(Continued)

*Primary Examiner* — Russell S Negin
(74) *Attorney, Agent, or Firm* — Kilpatrick Townsend & Stockton LLP

(57) ABSTRACT

Methods, systems and circuits evaluate a subject's CVD risk using a risk parameter that includes at least one HDL and inflammatory biomarker interaction parameter. The inflammatory biomarker may optionally comprise NMR derived measurements of GlycA from at least one biosample of the subject. The risk parameter may be gender-specific.

11 Claims, 34 Drawing Sheets

Related U.S. Application Data

(60) Provisional application No. 62/049,141, filed on Sep. 11, 2014.

(51) Int. Cl.
    *G01N 33/92*     (2006.01)
    *G01R 33/465*     (2006.01)
    *A61B 5/00*     (2006.01)
    *G16H 50/30*     (2018.01)

(52) U.S. Cl.
    CPC ..... *G01N 2570/00* (2013.01); *G01N 2800/32* (2013.01); *G16H 50/30* (2018.01)

(56) References Cited

U.S. PATENT DOCUMENTS

| | | |
|---|---|---|
| 2010/0100334 A1 | 4/2010 | Otvos |
| 2010/0179066 A1 | 7/2010 | Chapman et al. |
| 2013/0289884 A1 | 10/2013 | Otvos et al. |
| 2014/0088072 A1 | 3/2014 | Asztalos et al. |
| 2016/0077116 A1 | 3/2016 | Otvos et al. |

FOREIGN PATENT DOCUMENTS

| | | |
|---|---|---|
| CN | 101627306 | 1/2010 |
| CN | 101903777 | 12/2010 |
| CN | 102971633 | 3/2013 |
| CN | 104508471 | 4/2015 |
| CN | 107110939 | 8/2017 |
| EP | 2 592 423 | 5/2013 |
| EP | 3 177 939 | 6/2017 |
| JP | 2004226176 | 8/2004 |
| JP | 2005509860 | 4/2005 |
| JP | 2012506051 | 3/2012 |
| WO | WO 2007/133593 | 11/2007 |
| WO | 2011/138419 | 11/2011 |
| WO | WO 2011/153271 | 12/2011 |
| WO | WO 2013/184483 | 12/2013 |
| WO | 2016/040859 | 3/2016 |

OTHER PUBLICATIONS

Zhou, C. et al., Reduced paraoxonase 1 activity as a marker for severe coronary artery disease, Disease Markers, 2013, vol. 35(2), pp. 97-103.
Patent Cooperation Treaty, International Search Report and Written Opinion, International Application No. PCT/US2015/049778 dated Dec. 17, 2015.
Manickam, P. et al., "Sex and Ethnic Disparities in High-Density Lipoprotein Subclasses", J. Clinical Lipidology, 4(3):214-215 (2010).
Zhou, C. et al., "Reduced Paraoxonase 1 Activity as a Marker for Severe Coronary Artery Disease", Disease Markers, 35(2):97-103 (2013).
U.S. Appl. No. 14/852,192, Non-Final Office Action, dated Jul. 20, 2017, 12 pages.
U.S. Appl. No. 14/852,192, Notice of Allowance, dated Dec. 15, 2017, 8 pages.
CA 2,960,822, Office Action, dated Sep. 24, 2020, 5 pages.
CA 2,960,822, Office Action, dated Sep. 30, 2019, 6 pages.
CN 201580061390.6, Office Action, dated Mar. 28, 2019, 11 pages.
CN 201580061390.6, Office Action, dated Aug. 24, 2020, 12 pages.
CN 201580061390.6, Office Action, dated Jan. 13, 2020, 26 pages.
CN 201580061390.6, Notice of Decision to Grant, dated Feb. 9, 2021, 5 pages.
EP 15772098.8, Office Action, dated Nov. 10, 2020, 6 pages.
EP 15772098.8, Office Action, dated Apr. 9, 2019, 4 pages.
EP 15772098.8, Office Action, dated Mar. 16, 2018, 6 pages.
JP 2017-513725, Notice of Allowance, dated Dec. 1, 2020, 4 pages.
JP 2017-513725, Office Action, dated Dec. 17, 2019, 12 pages.
JP 2017-513725, Office Action, dated May 28, 2019, 12 pages.
JP 2017-513725, Office Action, dated Sep. 1, 2020, 4 pages.
JP 2019-189261, Office Action, dated Oct. 6, 2020, 4 pages.
PCT/US2015/049778, International Preliminary Report on Patentability, dated Mar. 23, 2017, 11 pages.
PCT/US2015/49778, International Search Report and Written Opinion, dated Dec. 17, 2015, 16 pages.

\* cited by examiner

| Parameter | | DF | Estimate | Standard Error | Wald Chi-Square | PR > ChiSq |
|---|---|---|---|---|---|---|
| Intercept | | 1 | -6.8359 | 2.1910 | 9.7344 | 0.0018 |
| Age | | 1 | 0.0531 | 0.00752 | 49.8925 | <.0001 |
| Gender | | 1 | 0.7403 | 0.1586 | 21.7789 | <.0001 |
| Race | 1 | 1 | 0.2931 | 0.1070 | 7.4957 | 0.0062 |
| Race | 2 | 1 | -0.3256 | 0.1836 | 3.1442 | 0.0762 |
| Race | 3 | 1 | -0.0843 | 0.1288 | 0.4278 | 0.5131 |
| SBP | | 1 | 0.0141 | 0.00300 | 22.0778 | <.0001 |
| Htnmed | | 1 | 0.4947 | 0.1388 | 12.6947 | 0.0004 |
| Smoking | | 1 | 0.4481 | 0.1909 | 5.5101 | 0.0189 |
| BMI | | 1 | 0.00174 | 0.0143 | 0.0147 | 0.9034 |
| DM | | 1 | 0.6576 | 0.1595 | 16.9919 | <.0001 |
| LDL-P | | 1 | 0.000507 | 0.000176 | 8.2685 | 0.0040 |
| TG | | 1 | 0.000738 | 0.000839 | 0.7749 | 0.3787 |
| HLP | | 1 | 0.2328 | 0.1258 | 3.4244 | 0.0642 |
| HMSP | | 1 | -0.2024 | 0.0671 | 9.1919 | 0.0026 |
| GlycA | | 1 | -0.00632 | 0.00571 | 1.2249 | 0.2684 |
| HLP*GlycA | | 1 | -0.00079 | 0.000380 | 4.3451 | 0.0371 |
| HMSP*GlycA | | 1 | 0.000499 | 0.000188 | 7.0604 | 0.0079 |

$$(H \times I)_{CVD} = (0.2328 \times HLP) - (0.2024 \times HMSP) - (0.0063 \times GlycA) - (0.00079 \times HLP \times GlycA) + (0.000499 \times HMSP \times GlycA)$$

FIG. 4

| Parameter | | DF | Estimate | Standard Error | Wald Chi-Square | PR > ChiSq |
|---|---|---|---|---|---|---|
| Intercept | | 1 | -16.8484 | 1.5487 | 118.3535 | <.0001 |
| Age | | 1 | 0.0531 | 0.00751 | 49.9748 | <.0001 |
| Gender | | 1 | .7426 | 0.1356 | 30.0057 | <.0001 |
| Race | 1 | 1 | 0.2930 | 0.1061 | 7.6336 | 0.0057 |
| Race | 2 | 1 | -0.3253 | 0.1823 | 3.1846 | 0.0743 |
| Race | 3 | 1 | -0.0846 | 0.1282 | 0.4349 | 0.5096 |
| SBP | | 1 | 0.0141 | 0.00299 | 22.2257 | <.0001 |
| Htnmed | | 1 | 0.4947 | 0.1384 | 12.7714 | 0.0004 |
| Smoking | | 1 | 0.4481 | 0.1900 | 5.5628 | 0.0183 |
| BMI | | 1 | 0.00180 | 0.0140 | 0.0166 | 0.8975 |
| DM | | 1 | 0.6577 | 0.1590 | 17.1058 | <.0001 |
| LDL-P | | 1 | 0.000508 | 0.000169 | 9.0341 | 0.0026 |
| TG | | 1 | 0.000741 | 0.000784 | 0.8944 | 0.3443 |
| HxI$_{CVD}$ | | 1 | 1.0005 | 0.2055 | 23.7081 | <.0001 |

FIG. 5

| Parameter | DF | Estimate | Standard Error | Wald Chi-Square | PR > ChiSq |
|---|---|---|---|---|---|
| Intercept | 1 | -5.9394 | 1.9795 | 9.0030 | 0.0027 |
| Age | 1 | 0.0530 | 0.00752 | 49.5509 | <.0001 |
| Gender | 1 | 0.8092 | 0.1451 | 31.0886 | <.0001 |
| Race 1 | 1 | 0.2940 | 0.1070 | 7.5430 | 0.0060 |
| Race 2 | 1 | -0.3078 | 0.1835 | 2.8145 | 0.0934 |
| Race 3 | 1 | -0.0971 | 0.1285 | .5712 | 0.4498 |
| SSP | 1 | 0.0137 | 0.00299 | 20.9928 | <.0001 |
| Htnmed | 1 | 0.4897 | 0.1386 | 12.4905 | 0.0004 |
| Smoking | 1 | 0.4593 | 0.1905 | 5.8115 | 0.0159 |
| BMI | 1 | 0.00459 | 0.0139 | 0.1082 | 0.7422 |
| DM | 1 | 0.6913 | 0.1586 | 19.0090 | <.0001 |
| LDL-P | 1 | 0.000552 | 0.000169 | 10.6461 | 0.0011 |
| TG | 1 | 0.00108 | 0.000809 | 1.7695 | 0.1834 |
| HMSP | 1 | -0.1989 | 0.0672 | 8.7691 | 0.0031 |
| GlycA | 1 | -0.00950 | 0.00529 | 1.2324 | 0.0722 |
| **HMSP*GlycA | 1 | 0.000472 | 0.000187 | 5.3951 | 0.0114** |

FIG. 9

| Parameter | | DF | Estimate | Standard Error | Wald Chi-Square | PR > ChiSq |
|---|---|---|---|---|---|---|
| Intercept | | 1 | -12.6241 | 1.1554 | 119.3820 | <.0001 |
| Age | | 1 | 0.0532 | 0.00754 | 49.8621 | <.0001 |
| Gender | | 1 | 0.7804 | 0.1549 | 25.3752 | <.0001 |
| Race | 1 | 1 | 0.2716 | 0.1060 | 6.5664 | 0.0104 |
| Race | 2 | 1 | -0.3096 | 0.1831 | 2.8592 | 0.0909 |
| Race | 3 | 1 | -0.0717 | 0.1287 | 0.3102 | 0.5776 |
| SBP | | 1 | 0.0137 | 0.003301 | 20.8143 | <.0001 |
| Htnmed | | 1 | 0.4880 | 0.1385 | 12.4050 | 0.0004 |
| Smoking | | 1 | 0.4670 | 0.1905 | 6.0097 | 0.0142 |
| BMI | | 1 | 0.00448 | 0.0143 | 0.0985 | 0.7536 |
| DM | | 1 | 0.6660 | 0.1589 | 17.5591 | <.0001 |
| LDL-P | | 1 | 0.000526 | 0.000177 | 8.8930 | 0.0029 |
| TG | | 1 | 0.000616 | 0.000826 | 0.5556 | 0.4561 |
| HLP | | 1 | 0.2905 | 0.1315 | 4.8826 | 0.0271 |
| GlycA | | 1 | 0.00788 | 0.00239 | 10.8890 | 0.0010 |
| HLP*GlycA | | 1 | -0.00095 | 0.000394 | 5.7889 | 0.0161 |

FIG. 11

| Parameter | DF | Estimate | Standard Error | Wald Chi-Square | Pr > ChiSq |
|---|---|---|---|---|---|
| Intercept | 1 | -9.7485 | 0.6950 | 196.7441 | <.0001 |
| age | 1 | 0.0556 | 0.00573 | 94.2283 | <.0001 |
| race  1 | 1 | 0.3668 | 0.0844 | 18.8906 | <.0001 |
| race  2 | 1 | -0.3644 | 0.1497 | 5.9252 | 0.0149 |
| race  3 | 1 | -0.0491 | 0.1001 | 0.2412 | 0.6234 |
| gender | 1 | 0.7506 | 0.1117 | 45.1518 | <.0001 |
| smoking | 1 | 0.5702 | 0.1489 | 14.6702 | 0.0001 |
| hypertension | 1 | 0.7895 | 0.1143 | 47.7042 | <.0001 |
| diabetes | 1 | 0.5782 | 0.1305 | 19.6436 | <.0001 |
| BMI | 1 | 0.007742 | 0.0110 | 0.4592 | 0.4980 |
| LDL-P | 1 | 0.000398 | 0.000139 | 8.2148 | 0.0042 |
| VLDL-P | 1 | 0.000745 | 0.00104 | 0.5170 | 0.4721 |
| GlycA | 1 | 0.00489 | 0.00124 | 15.5057 | <.0001 |
| H8 | 1 | 1.5270 | 0.5269 | 8.3974 | 0.0038 |
| **GlycA*H8** | 1 | -0.00512 | 0.00172 | 8.8146 | 0.0030 |

$(H8xI)_{CVD}$ = (GlycA*0.00489) + (H8*1.527) − (GlycA*H8*0.00512) + 5

FIG. 14

| Parameter | | DF | Estimate | Standard Error | Wald Chi-Square | Pr > ChiSq |
|---|---|---|---|---|---|---|
| Intercept | | 1 | -6.2667 | 1.0297 | 37.0413 | <.0001 |
| age | | 1 | 0.0547 | 0.00575 | 90.4737 | <.0001 |
| race | 1 | 1 | 0.3727 | 0.0846 | 19.4112 | <.0001 |
| race | 2 | 1 | -0.3433 | 0.1497 | 5.2566 | 0.0219 |
| race | 3 | 1 | -0.0356 | 0.1009 | 0.1245 | 0.7242 |
| gender | | 1 | 0.7502 | 0.1117 | 45.0668 | <.0001 |
| smoking | | 1 | 0.5672 | 0.1499 | 14.3105 | 0.0002 |
| hypertension | | 1 | 0.7760 | 0.1145 | 45.9640 | <.0001 |
| diabetes | | 1 | 0.5767 | 0.1307 | 19.4618 | <.0001 |
| BMI | | 1 | 0.0109 | 0.0107 | 1.0245 | 0.3115 |
| LDL-P | | 1 | 0.000448 | 0.000136 | 10.9089 | 0.0010 |
| VLDL-P | | 1 | 0.00114 | 0.00102 | 1.2524 | 0.2631 |
| GlycA | | 1 | -0.00568 | 0.00251 | 5.1100 | 0.0238 |
| H1 | | 1 | -0.5255 | 0.1460 | 12.9655 | 0.0003 |
| **GlycA*H1 | | 1 | 0.00148** | 0.000409 | 13.1383 | 0.0003 |

$(H1xI)_{CVD} = -(GlycA*0.00568) - (H1*0.5255) + (GlycA*H1*0.00148) + 5$

FIG. 15

| Parameter | | DF | Estimate | Standard Error | Wald Chi-Square | Pr > ChiSq |
|---|---|---|---|---|---|---|
| Intercept | | 1 | -15.5697 | 2.1170 | 54.0919 | <.0001 |
| age | | 1 | 0.0555 | 0.00574 | 93.4862 | <.0001 |
| race | 1 | 1 | 0.3786 | 0.0847 | 19.9908 | <.0001 |
| race | 2 | 1 | -0.3362 | 0.1497 | 5.0429 | 0.0247 |
| race | 3 | 1 | -0.0563 | 0.1008 | 0.3116 | 0.5767 |
| gender | | 1 | 0.6798 | 0.1199 | 32.1579 | <.0001 |
| smoking | | 1 | 0.5570 | 0.1493 | 13.9077 | 0.0002 |
| hypertension | | 1 | 0.7904 | 0.1148 | 47.3642 | <.0001 |
| diabetes | | 1 | 0.5612 | 0.1310 | 18.3442 | <.0001 |
| BMI | | 1 | 0.00699 | 0.0108 | 0.4184 | 0.5177 |
| LDL-P | | 1 | 0.000397 | 0.000137 | 8.4017 | 0.0037 |
| VLDL-P | | 1 | 0.000710 | 0.00104 | 0.4675 | 0.4941 |
| GlycA | | 1 | -0.00192 | 0.00152 | 1.6048 | 0.2052 |
| H2-7 | | 1 | -0.0255 | 0.0157 | 2.6418 | 0.1041 |
| (H8xI)cvd | | 1 | 0.8782 | 0.3416 | 6.6110 | 0.0101 |
| (H1xI)cvd | | 1 | 0.9224 | 0.2749 | 11.2625 | 0.0008 |

$(HxI)_{CVD}$ is the brace grouping of H2-7, (H8xI)cvd, (H1xI)cvd $(HxI)_{CVD} = ((H8xI)_{CVD}*0.8782) + ((H1xI)_{CVD}*0.9224) - (H2\text{-}7*0.0255)$

FIG. 16

| Model | | Model | | Parameter | | |
|---|---|---|---|---|---|---|
| | Parameters | LR $\chi^2$ | $\Delta \chi^2$ | $\chi^2$ | sign | p |
| 1 | Base Model | 351.0 | --- | --- | --- | --- |
| 2 | LDL-C | 359.4 | 8.4 | 12.1 | + | 0.0005 |
| | HDL-C | | | 5.3 | − | 0.02 |
| 3 | LDL-C | 367.3 | 16.3 | 11.8 | + | 0.0006 |
| | HDL-C | | | 5.4 | − | 0.02 |
| | hs-CRP | | | 5.4 | + | 0.02 |
| 4 | LDL-P | 359.7 | 8.7 | 8.8 | + | 0.003 |
| 5 | LDL-P | 365.4 | 14.4 | 7.2 | + | 0.007 |
| | HDL-P | | | 5.6 | − | 0.02 |
| 6 | LDL-P | 375.7 | 24.7 | 7.0 | + | 0.008 |
| | HDL-P | | | 6.8 | − | 0.009 |
| | GlycA | | | 10.7 | + | 0.001 |
| 7 | LDL-P | 381.7 | 30.7 | 7.5 | + | 0.006 |
| | (H8xl)$_{CVD}$ | | | 40.4 | + | <0.0001 |
| 8 | LDL-P | 382.1 | 31.1 | 9.3 | + | 0.002 |
| | (H1xl)$_{CVD}$ | | | 26.6 | + | <0.0001 |
| 9 | LDL-P | 392.2 | 41.2 | 7.7 | + | 0.005 |
| | (H8xl)$_{CVD}$ | | | 15.2 | + | <0.0001 |
| | (H1xl)$_{CVD}$ | | | 11.7 | + | 0.0006 |
| 10 | LDL-P | 395.6 | 44.6 | 6.5 | + | 0.01 |
| | (H8xl)$_{CVD}$ | | | 12.6 | + | 0.0004 |
| | (H1xl)$_{CVD}$ | | | 12.5 | + | 0.0004 |
| | H2-7 | | | 3.4 | − | 0.07 |
| 11 | LDL-P | 395.2 | 44.2 | 6.8 | + | 0.009 |
| | (Hxl)$_{CVD}$ | | | 49.7 | + | <0.0001 |

FIG. 18

| | Parameter | | DF | Estimate | Standard Error | Wald Chi-Square | Pr > ChiSq |
|---|---|---|---|---|---|---|---|
| | Intercept | | 1 | -10.1677 | 1.2578 | 65.3485 | <.0001 |
| | age | | 1 | 0.0741 | 0.00952 | 60.5995 | <.0001 |
| | race | 1 | 1 | 0.4455 | 0.1376 | 10.4867 | 0.0012 |
| | race | 2 | 1 | -0.2088 | 0.2385 | 0.7662 | 0.3814 |
| | race | 3 | 1 | -0.0617 | 0.1625 | 0.1440 | 0.7043 |
| | smoking | | 1 | 0.6974 | 0.2518 | 7.6709 | 0.0056 |
| | hypertension | | 1 | 0.7384 | 0.1911 | 14.9260 | 0.0001 |
| | diabetes | | 1 | 0.4460 | 0.2223 | 4.0263 | 0.0448 |
| | BMI | | 1 | 0.0122 | 0.0158 | 0.6026 | 0.4376 |
| | LDL-P | | 1 | 0.000172 | 0.000220 | 0.6091 | 0.4351 |
| | VLDL-P | | 1 | 0.000362 | 0.00169 | 0.0461 | 0.8299 |
| $(HxI)^W$ | GlycA | | 1 | 0.00558 | 0.00197 | 8.0707 | 0.0045 |
| | H8 | | 1 | 1.6708 | 0.6339 | 6.9482 | 0.0084 |
| | **GlycA*H8** | | 1 | -0.00551 | 0.00211 | 6.7851 | 0.0092 |
| | HDL-P | | 1 | -0.0350 | 0.0268 | 1.6973 | 0.1926 |

$$(HxI)^W = (GlycA*0.00558) + (H8*1.6708) - (GlycA*H8*0.00551) - (HDL\text{-}P*0.035) + 5$$

FIG. 21

| Parameter | DF | Estimate | Standard Error | Wald Chi-Square | Pr > ChiSq |
|---|---|---|---|---|---|
| Intercept | 1 | -3.5106 | 1.5026 | 5.45585 | 0.0195 |
| age | 1 | 0.0448 | 0.00727 | 37.9647 | <.0001 |
| race 1 | 1 | 0.3305 | 0.1090 | 9.1939 | 0.0024 |
| race 2 | 1 | -0.4332 | 0.1948 | 4.9440 | 0.0262 |
| race 3 | 1 | -0.0222 | 0.1295 | 0.0295 | 0.8636 |
| smoking | 1 | 0.4323 | 0.1893 | 5.2167 | 0.0224 |
| hypertension | 1 | 0.8111 | 0.1449 | 31.3385 | <.0001 |
| diabetes | 1 | 0.6190 | 0.1644 | 14.1828 | 0.0002 |
| BMI | 1 | 0.00240 | 0.0159 | 0.0229 | 0.8796 |
| LDL-P | 1 | 0.000506 | 0.000179 | 7.9941 | 0.0047 |
| VLDL-P | 1 | 0.000479 | 0.00134 | 0.1280 | 0.7205 |
| GlycA | 1 | -0.00704 | 0.00347 | 4.1291 | 0.0422 |
| H1 | 1 | -0.5898 | 0.1881 | 9.8351 | 0.0017 |
| **GlycA*H1 | 1 | 0.00173 | 0.000546 | 10.0018 | 0.0016** |
| HDL-P | 1 | -0.0403 | 0.0237 | 2.8790 | 0.0897 |

The bracketed rows (GlycA, H1, GlycA*H1) are denoted $(H \times I)^M$.

FIG. 22

$$(H \times I)^M = -(GlycA * 0.00704) - (H1 * 0.5898) + (GlycA * H1 * 0.00173) - (HDL\text{-}P * 0.0403) + 5$$

| Model | Parameters | Model LR $\chi^2$ | Model $\Delta \chi^2$ | Parameter sign | Parameter $\chi^2$ | Parameter p |
|---|---|---|---|---|---|---|
| 1 | Base Model | 145.4 | --- | --- | --- | --- |
| 2 | LDL-C | 149.3 | 3.9 | + | 2.7 | 0.10 |
|   | HDL-C |   |   | − | 1.4 | 0.23 |
| 3 | LDL-C | 151.5 | 6.1 | + | 2.8 | 0.09 |
|   | HDL-C |   |   | − | 1.6 | 0.20 |
|   | hs-CRP |   |   | + | 1.2 | 0.27 |
| 4 | LDL-P | 145.7 | 0.3 | + | 0.3 | 0.57 |
| 5 | LDL-P | 149.1 | 3.7 | + | 0.2 | 0.68 |
|   | HDL-P |   |   | − | 3.3 | 0.07 |
| 6 | LDL-P | 151.7 | 6.3 | + | 0.1 | 0.76 |
|   | HDL-P |   |   | − | 4.2 | 0.04 |
|   | GlycA |   |   | + | 2.8 | 0.10 |
| 7 | LDL-P | 162.0 | 16.6 | + | 0.1 | 0.73 |
|   | (HxI)$^W$ |   |   | + | 32.8 | <0.0001 |
| 8 | LDL-P | 164.2 | 18.8 | + | 0.04 | 0.84 |
|   | (HxI)$^W$ |   |   | + | 16.4 | <0.0001 |
|   | (HxI)$^M$ |   |   | + | 2.3 | 0.13 |

FIG. 26

| Model | | Model | | Parameter | | |
|---|---|---|---|---|---|---|
| | Parameters | LR $\chi^2$ | $\Delta \chi^2$ | sign | $\chi^2$ | p |
| 1 | Base Model | 168.1 | -- | -- | -- | -- |
| 2 | LDL-C | 181.7 | 13.6 | + | 10.7 | 0.001 |
| | HDL-C | | | − | 4.8 | 0.03 |
| 3 | LDL-C | 186.4 | 18.3 | + | 10.0 | 0.002 |
| | HDL-C | | | − | 4.4 | 0.04 |
| | hs-CRP | | | + | 4.2 | 0.04 |
| 4 | LDL-P | 175.4 | 7.3 | + | 7.4 | 0.006 |
| 5 | LDL-P | 178.1 | 10.0 | + | 6.5 | 0.01 |
| | HDL-P | | | − | 2.7 | 0.10 |
| 6 | LDL-P | 186.7 | 18.6 | + | 6.6 | 0.01 |
| | HDL-P | | | − | 2.8 | 0.09 |
| | GlycA | | | + | 9.0 | 0.003 |
| 7 | LDL-P | 198.0 | 29.9 | + | 5.7 | 0.02 |
| | (HxI)$^M$ | | | + | 25.2 | <0.0001 |
| 8 | LDL-P | 198.4 | 30.3 | + | 5.4 | 0.02 |
| | (HxI)$^M$ | | | + | 12.6 | 0.0004 |
| | (HxI)$^W$ | | | + | 0.4 | 0.54 |

FIG. 27

| Parameter | Women | | Men | |
| --- | --- | --- | --- | --- |
| | $\chi^2$ | p | $\chi^2$ | p |
| Age | 63.2 | <0.0001 | 45.8 | <0.0001 |
| Smoking | 10.3 | 0.001 | 6.6 | 0.01 |
| Hypertension | 16.6 | <0.0001 | 30.2 | <0.0001 |
| Diabetes | 4.7 | 0.03 | 15.1 | 0.0001 |
| BMI | 0.4 | 0.73 | 0.0 | 0.96 |
| $(HxI)^W$ | 32.7 | <0.0001 | --- | --- |
| $(HxI)^M$ | --- | --- | 25.2 | <0.0001 |

FIG. 28

(Semi) Automated Risk Calculator

Gender ☐
Age (yrs) ☐
LDL-P ☐
(Hxl)CVD ☐
Smoking? ☐
HDL-P ☐
Type 2 DM? ☐
Inflammatory biomarker ☐

Treatment:
HPT ☐
BP ☐
Systolic BP ☐

CVD Risk ☐

FIG. 29A

(Semi) Automated Risk Calculator

Gender ☐
Age (yrs) ☐
Systolic BP ☐
(Hxl)$_{CVD}$ ☐
LDL-P ☐

CVD Risk ☐

FIG. 29B

CARDIOVASCULAR RISK EVALUATIONS USING A RISK PARAMETER THAT INCLUDES AN HDL AND INFLAMMATORY BIOMARKER INTERACTION PARAMETER

RELATED APPLICATIONS

The present application is a continuation of U.S. patent application Ser. No. 14/852,192, filed Sep. 11, 2015, which claims priority to U.S. Provisional Patent Application No. 62/049,141, filed Sep. 11, 2014. The disclosure of each of these applications is hereby incorporated by reference in their entireties herein.

FIELD

The present invention relates generally to analysis of in vitro biosamples.

BACKGROUND

Lipoproteins include a wide variety of particles found in plasma, serum, whole blood, and lymph, comprising various types and quantities of triglycerides, cholesterol, phospholipids, sphyngolipids, and proteins. These various particles permit the solubilization of otherwise hydrophobic lipid molecules in blood and serve a variety of functions related to lipolysis, lipogenesis, and lipid transport between the gut, liver, muscle tissue and adipose tissue. Inflammation can be associated with many different disease states. See, e.g., Fogelman, When Good Cholesterol Goes Bad, *Nature Medicine* (2004) 10(9): 902-903, Hima Bindu G et al., Friend Turns Foe: Transformation of Anti-Inflammatory HDL to Proinflammatory HDL during Acute-Phase Response, *Cholesterol* (2011) 2011: Article ID 274629 (7 pages), the contents of which are hereby incorporated by reference as if recited in full herein. Carbohydrate components of glycoproteins can perform biological functions in protein sorting, immune and receptor recognition, inflammation and other cellular processes. It is believed that inflammation may modulate HDL functionality.

Conventionally, a patient's overall risk of coronary heart disease (CHD) and/or cardiovascular disease (CVD) has been assessed based on measurements of cholesterol content of a patient's LDL and HDL particles, denoted as LDL cholesterol (LDL-C) or HDL cholesterol (HDL-C), rather than the numbers of these particles. These two risk factors are often used to assess a patient's risk, and treatment decisions may be made to reduce the "bad" cholesterol (LDL-C) or increase the "good" cholesterol (HDL-C).

On the other hand, advanced lipoprotein test panels have typically included a total High Density Lipoprotein Particle (HDL-P) measurement (e.g., HDL-P number) and a total Low Density Lipoprotein Particle (LDL-P) measurement (e.g., LDL-P number). The particle numbers represent the concentration in concentration units such as nmol/L. The total HDL-P number may be the sum of the concentration values of each of the sub-groups of HDL-P subclasses, e.g., small, medium and large.

It is believed that LDL-P is a better indicator of LDL-related risk of CHD and CVD relative to LDL-C and/or to guide therapy decisions. However, there are still open questions about the different functions of HDL and how to best evaluate CVD and/or CHD risk associated with a patient's HDL. See, e.g., Kher at el., Cholesterol Efflux Capacity, High-Density Lipoprotein Function, and Atherosclerosis, *N Engl. J. Med.* (2011) 364: 127-135; Navab et al., HDL and cardiovascular disease: atherogenic and atheroprotective mechanisms, *Nat. Rev. Cardiol.*, 8, 222-232 (2011); and Fogelman A, When good cholesterol goes bad, *Nat. Med.* (2004) 10(9): 902-903, the contents of which are hereby incorporated by reference as if recited in full herein.

The mechanisms by which HDL can be protective or non-protective as associated with a person's risk of developing atherosclerosis or heart disease are complex and multifactorial. See, Farmer et al., Evolving Concepts of the Role of High-Density Lipoprotein in Protection from Atherosclerosis, *Curr Atheroscler Rep* (2011) 13:107-114, and Hima Bindu G et al., Friend Turns Foe: Transformation of Anti-Inflammatory HDL to Proinflammatory HDL during Acute-Phase Response, *Cholesterol* (2011) 2011: Article ID 274629, 7 pages, the contents of which are hereby incorporated by reference as if recited in full herein.

The Framingham study proposed a relatively lengthy risk model that considers many factors such as age, gender, blood pressure, smoking habits, as well as cholesterol values. The research conducted in the Framingham Offspring Study also defined normative and at-risk population values from subjects in the study. See Wilson et al., *Impact of National Guidelines for Cholesterol Risk Factor Screening. The Framingham Offspring Study*, JAMA, 1989; 262: 41-44.

There remains a need for evaluations that can better predict or assess a person's cardiovascular risk and/or provide risk parameters that can be used for HDL therapy targets.

SUMMARY

The invention described herein includes method of determining a risk parameter for cardiovascular disease or events, including steps of obtaining measurements of HDL particles and at least one inflammatory biomarker in a biosample from a subject; determining concentrations for at least one individual HDL particle size subclass and the at least one inflammatory biomarker, based on the measurements; and programmatically calculating a risk parameter (($HxI)_{CVD}$) of the subject using at least the concentrations for the at least one subclass of HDL particle and the at least one inflammatory biomarker.

In some embodiments, the measurements are obtained by obtaining an NMR signal of an in vitro blood plasma or serum patient sample to determine NMR derived concentration measurements of the HDL particle subclasses and/or the inflammatory biomarker.

In some embodiments, HDL particles are analyzed in 8 different subclasses or subpopulations based on diameter. In other embodiments, HDL particles are analyzed in 20 or more different subclasses, or in other sub-groupings.

In some embodiments, the at least one individual HDL particle size subclass comprises at least one of the following: (i) cH1 having a diameter in the range of 7.0-7.6 nm; or (ii) cH8 having a diameter in the range of 11.5-13.5 nm.

In some embodiments, $(HxI)_{CVD}$ is: $(HxI)_{CVD}=c_1(cH1)+c_2(INFLAM)+c_3(INTER_{H1})$; or $(HxI)_{CVD}=c_4(cH8)+c_5(INFLAM)+c_6(INTER_{H8})$, wherein INFLAM is the concentration of the at least one inflammatory biomarker, $INTER_{H1}=INFLAM*cH1$, $INTER_{H8}=INFLAM*cH8$, and wherein "$c_1$-$c_6$" represent coefficients from a mathematical model of CVD events in a study population for the associated risk parameter.

In some embodiments, $(HxI)_{CVD}$ is gender-specific. In some embodiments, utilizing the concentration of an HDL-P subclass cH1, having an average diameter in the range of 7.0-7.6 nm, with GlycA as the inflammatory biomarker to generate $(HxI)_{CVD}$ provides a male-specific HDL-inflammation multimarker. In other embodiments, utilizing the concentration of an HDL-P subclass cH8, having an average diameter in the range of 11.5-13.5 nm, with GlycA as the inflammatory biomarker to generate $(HxI)_{CVD}$ provides a female-specific HDL-inflammation multimarker.

In some embodiments, methods further comprise electronically providing the calculated $(HxI)_{CVD}$ to a medical professional and/or patient report. In some embodiments, methods further comprise prescribing, recommending, or deciding upon a treatment for the subject based at least in part on the calculated $(HxI)_{CVD}$. In some embodiments, methods further comprise modification of the subject's diet, exercise, smoking, or other behaviors.

Some embodiments include systems, computer readable media, circuits, NMR spectrometers or NMR analyzers, online semi-automated risk calculators and processors that evaluate a person's CVD risk using the methods described herein. That is, the systems, computer readable media, circuits, NMR analyzers, semi-automated risk calculators, or processors obtain and utilize measurements of defined parameters from an in vitro blood plasma or serum patient sample using a defined multi-component risk progression model that includes at least one HDL and at least one inflammatory biomarker interaction parameter.

For example, some embodiments comprise a system that includes a component for obtaining measurements of HDL particles and at least one inflammatory biomarker in a biosample from a subject; a component for determining concentrations for at least one individual HDL particle size subclass and the at least one inflammatory biomarker, based on the measurements; and a component for programmatically calculating a risk parameter $((HxI)_{CVD})$ of the subject using at least the concentrations for the at least one subclass of HDL particle and the at least one inflammatory biomarker.

In some embodiments, the system is configured to calculate an $(HxI)_{CVD}$ risk parameter and/or monitor the $(HxI)_{CVD}$ risk parameter as a therapeutic target for either (a) raising or lowering HDL-P values or (b) lowering inflammation, or both (a) and (b). In some embodiments, the system is configured to calculate a measurement of GlycA multiplied by a concentration of a defined subpopulation of high density lipoprotein particles (HDL-P). In some embodiments, the at least one interaction parameter is GlycA multiplied by a concentration of an HDL-P subclass that demonstrates gender specificity for CVD events in a study population for the associated risk parameter.

In some embodiments, the component for obtaining measurements comprises an NMR analyzer. Some embodiments comprise non-transitory computer readable media for determining a risk parameter for cardiovascular disease or events according to the methods described herein. Some embodiments comprise a semi-automated risk calculator that evaluates a subject's CVD risk using the methods described herein.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with other embodiments although not specifically discussed therewith. That is, it is noted that aspects of the invention described with respect to one embodiment, may be incorporated in a different embodiment although not specifically described relative thereto. That is, all embodiments and/or features of any embodiment can be combined in any way and/or combination. Also, each of the embodiments of the methods of the invention may be incorporated into systems and computer program products of the invention and vice versa. The foregoing and other aspects of the present invention are explained in detail in the specification set forth below.

As will be appreciated by those of skill in the art in light of the present disclosure, embodiments of the present invention may include methods, systems, apparatus and/or computer program products or combinations thereof.

BRIEF DESCRIPTION OF THE FIGURES

FIG. 4 is a chart of risk parameters illustrating two interaction parameters, (HLP*GlycA) and (HMSP*GlycA), each comprising an HDL constituent with inflammatory biomarker GlycA that can be combined with the individual markers to yield the $(HxI)_{CVD}$ risk parameter according to some embodiments of the present invention.

FIG. 5 is a chart of CVD risk parameters showing $(HxI)_{CVD}$ is associated with CVD risk at least as strongly as major established CVD risk factors (from logistic regression model for CVD events (n=274) in MESA participants (n=5534) during five years of follow-up) according to embodiments of the present invention.

FIG. 9 is a chart illustrating logistic regression model parameters and values used to calculate predicted probabilities of a CVD event when using an interaction parameter (HxI), comprising one HDL parameter and one inflammation parameter (HMSP*GlycA) and only small and medium HDL-P subclasses (i.e., HMSP) according to embodiments of the present invention.

FIG. 11 is a chart illustrating logistic regression model parameters and values used to calculate predicted probabilities of a CVD event (percent) when using an interaction parameter comprising one HDL and one inflammation marker (HLP*GlycA), the inflammation marker (GlycA), and only large HDL-P subclasses (i.e., HLP) according to embodiments of the present invention.

FIG. 14 is a chart of risk parameters illustrating an interaction parameter, HDL constituent 8 (cH8 or H8) with an inflammatory biomarker (GlycA), or (GlycA*H8), that can provide an $(H8xI)_{CVD}$ risk parameter according to some embodiments of the present invention.

FIG. 15 is a chart of risk parameters illustrating an interaction parameter, HDL constituent 1 (cH1 or H1) with an inflammatory biomarker (GlycA), or (GlycA*H1), that can provide an $(H1xI)_{CVD}$ risk parameter according to some embodiments of the present invention.

FIG. 16 is a chart of risk parameters illustrating a multi-marker that comprises both interaction parameters shown in FIGS. 14 and 15, $(H8xI)_{CVD}$ and $(H1xI)_{CVD}$, as well as the remaining HDL constituents (H2-7), to provide an $(HxI)_{CVD}$ risk multimarker according to some embodiments of the present invention.

FIG. 18 is a chart illustrating CVD risk associations (as indicated by the model's likelihood ratio χ2 statistic (LR χ2)) for each of eleven different logistic regression models (all models have the same parameters as the base logistic regression model for incident CVD events in MESA (n=458/5660), adjusted for age, sex, race, smoking, hypertension, BMI, diabetes, BMI, and VLDL-P) showing the increased χ2 with the $(H8xI)_{CVD}$, $(H1xI)_{CVD}$, and $(HxI)_{CVD}$ risk parameters included in the model according to embodiments of the present invention.

FIG. 21 is a chart of risk parameters illustrating a female-specific interaction parameter, the $(HxI)^W$ CVD multimarker for women, that includes HDL constituent 8 (H8) and inflammatory biomarker GlycA, according to some embodiments of the present invention.

FIG. 22 is a chart of risk parameters illustrating a male-specific interaction parameter, the $(HxI)^M$ CVD multimarker for men, that includes HDL constituent 1 (H1) and inflammatory biomarker GlycA, according to some embodiments of the present invention.

FIG. 26 is a chart illustrating contribution of the $(HxI)^W$ multimarker to prediction of incident CVD in women (as indicated by the model's likelihood ratio (LR) $\chi2$ statistic) for each of eight different logistic regression models (all models have the same parameters as the base logistic regression model for incident CVD events in MESA (n=169/2868), adjusted for age, sex, race, smoking, hypertension, BMI, diabetes, and VLDL-P) showing the increased $\chi2$ with the $(HxI)^W$ risk parameter included models 7 and 8, according to embodiments of the present invention.

FIG. 27 is a chart illustrating contribution of the $(HxI)^M$ multimarker to prediction of incident CVD in men (as indicated by the model's likelihood ratio (LR) $\chi2$ statistic) for each of eight different logistic regression models (all models have the same parameters as the base logistic regression model for incident CVD events in MESA (n=282/2722), adjusted for age, sex, race, smoking, hypertension, BMI, diabetes, and VLDL-P) showing the increased $\chi2$ with the $(HxI)^M$ risk parameter included in models 7 and 8, according to embodiments of the present invention.

FIG. 28 is a chart illustrating contributions of the $(HxI)^W$ and $(HxI)^M$ gender-specific multimarkers to CVD risk prediction, as compared to traditional risk factors.

FIGS. 29A and 29B are exemplary risk calculators that may be electronically provided for use on the internet by individuals or clinicians according to embodiments of the present invention.

Figure 1:
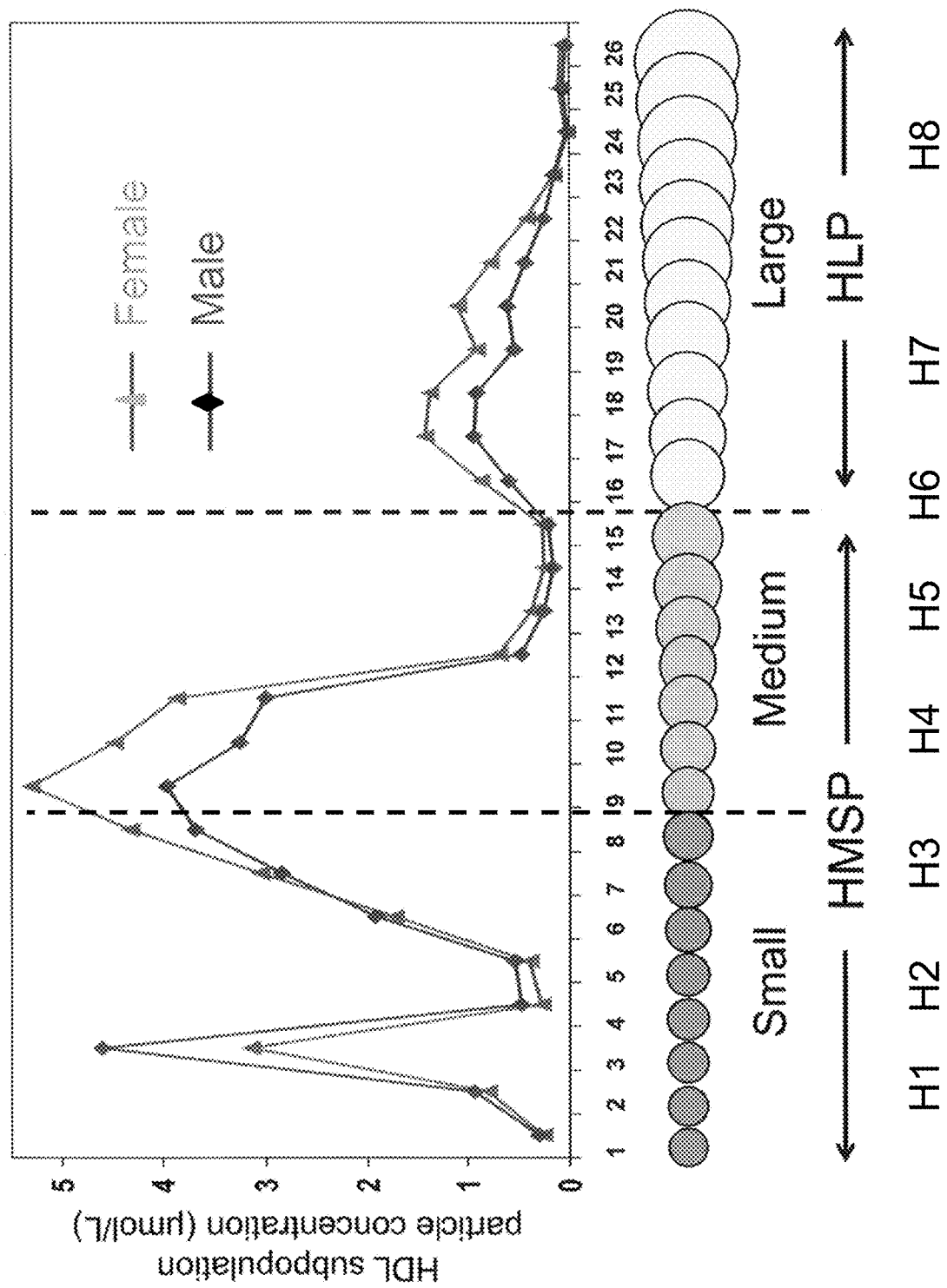
FIG. 1 is a graph of mean concentrations (μmol/L) of HDL-P subpopulations in the Multi-Ethnic Study of Atherosclerosis (MESA) for female (triangle annotated line) and male (diamond annotated line) subjects. Particle sizes are shown in increments 1-26 by diameter, grouped as exemplary small, medium and large HDL-P sub-classes, or alternatively grouped as H1-H8.

The foregoing and other objects and aspects of the present invention are explained in detail in the specification set forth below.

DETAILED DESCRIPTION OF EMBODIMENTS OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "programmatically" means carried out using computer program and/or software, processor or ASIC directed operations. The term "electronic" and derivatives thereof refer to automated or semi-automated operations carried out using devices with electrical circuits and/or modules rather than via mental steps and typically refers to operations that are carried out programmatically. The terms "automated" and "automatic" means that the operations can be carried out with minimal or no manual labor or input. The term "semi-automated" refers to allowing operators or users some input or activation, but the calculations and signal acquisition as well as the calculation of the concentrations or numerical outputs are done electronically, typically programmatically, without requiring manual input.

The term "about" refers to +/−10% (mean or average) of a specified value or number.

The term "patient" is used broadly and refers to an individual or animal subject that provides a biosample for testing or analysis.

The term "biosample" refers to in vitro blood, plasma or serum samples of humans or animals. Or it may refer to other types of samples from living subjects. Embodiments of the invention may be particularly suitable for evaluating human blood plasma or serum samples. The blood plasma or serum samples may be fasting or non-fasting.

The terms "population norm" and "standard" refer to values defined by a large study or studies such as the Framingham Offspring Study or the Multi-Ethnic Study of Atherosclerosis (MESA) or other study having a large enough sample to be representative of a general population. However, the instant invention is not limited to the population values in MESA or Framingham, as the presently defined normal and at-risk population values or levels may change over time. Thus, a reference range or statistical coefficient number provided by way of example in this document may change as will be well known to those of skill in the art based on a different study population. The term "cardiovascular disease" generally refers to conditions that involve narrowed or blocked blood vessels that can lead to a heart attack, chest pain (angina), stroke, or death.

The terms "mathematical model" and "model" are used interchangeably and when used with "CVD" risk, refer to a statistical model of risk used to evaluate a subject's CVD risk in the future, typically within 2-10 years. The risk model can be or include any suitable model including, but not limited to, one or more of a logistic model, proportional hazards (Cox) model, a mixed model or a hierarchical linear model. The risk model can be evaluated on the basis of a model discrimination statistic, such as the likelihood ratio (LR) $\chi 2$ value or the c-statistic (also called the AUC value). The relative contribution of a given variable in the model to the model's overall prediction is typically estimated by the Wald $\chi 2$ value and/or the p value (the latter with a sufficiently representative study population).

The term "interaction parameter" as used herein refers to a term that represents the interaction between two variables, wherein one modulates the other with respect to a third variable, e.g., the interaction between an HDL subpopulation and an inflammatory biomarker with respect to CVD events, or $(HxI)_{CVD}$. The term may comprise a combination (e.g., a multiplied product or ratio) of the interacting variables.

The term "multimarker" as used herein refers to a term that comprises a combination (e.g., a multiplied product or ratio) of two or more biomarker parameters.

A. HDL Particle Subpopulation and Inflammatory Marker Detection by NMR

The role of HDL is complex and HDL cholesterol (HDL-C) is considered to be a relatively crude biomarker. As is generally accepted, HDL-cholesterol and/or LDL-cholesterol levels provided by conventional lipid panels fail to sufficiently differentiate populations with and without elevated risk for CHD or CVD.

Embodiments of the invention provide risk assessments of a subject's cardiovascular (CVD) risk comprising calculating one or more HDL and inflammatory biomarker interaction parameters.

In blood and/or plasma, HDL has been classified in many ways, generally based on physical properties such as density or electrophoretic mobility or measures of apolipoprotein A-1 (Apo A-1), the main protein in HDL.

Embodiments of the invention classify lipoprotein particles into subclasses grouped by size ranges based on functional/metabolic relatedness as assessed by their correlations with lipid and metabolic variables as shown in the example of FIG. 1.

A biosample can be evaluated to measure over 20 discrete subpopulations (sizes) of lipoprotein particles, typically between about 30-80 different size subpopulations (or even more). These discrete sub-populations can be grouped into defined subclasses. The defined subclasses can include a plurality of different subclasses, including three each for VLDL and HDL and two or three for LDL (if the latter, with one of the three identified as IDL in the size range between large LDL and small VLDL). The different subclasses typically include different numbers of sub-populations or components of different particle sizes within the subclass groupings. The large HDL subclass can include more discrete subpopulation measurements than either the medium or small HDL subclasses. The medium HDL subclass can include less sub-population components or measurements than either the large HDL or small HDL subclasses. Each of the HDL subclass groupings can include greater than five (5) discrete subpopulation measurements. There can be nine (9) different subclasses, three each (small, medium, large) for the VLDL, LDL and HDL subclasses, although other groupings may be used.

In some embodiments, as shown in FIG. 1, the lipoprotein measurements can include 26 size subpopulations for HDL-P. Alternatively, the lipoprotein measurements can include 8 size subpopulations for HDL-P, also shown in FIG. 1 and described further in part C herein. However, other groupings, size ranges for a grouping, and/or numbers of discrete sub-population measurements may be used. In the embodiment shown in FIG. 1, the different subpopulations of HDL-P can be identified by a number from 1-26, with "1" representing the smallest size HDL subpopulation and "26" being the largest size HDL subpopulation; or the different subpopulations of HDL-P can be identified by a number from H1-H8, with "H1" representing the smallest size HDL subpopulation and "H8" being the largest size HDL subpopulation. FIG. 1 shows the mean concentrations of HDL-P subclasses in MESA male and female subjects. As described in detail below, in some embodiments, the HDL particles are defined as 8, rather than 26, subpopulations or subclasses. The use of subclasses H1-H8 is described further in part C below. Alternatively HDL particles may be grouped differently by size (or other features or characteristics).

In some embodiments, the total number of components (subpopulations or subclasses) of HDL lipoprotein particles can be about 26, with the small HDL components including 1-8, the medium HDL components including 9-15 and the large HDL components including 16-26. However, the upper end of one grouping may be included in the lower end of the adjacent grouping and vice versa. Also, one or more subclasses in a particular grouping can be omitted for the calculation, e.g., 26 may be omitted from the large HDL-P grouping or 8 may be omitted from the small or medium HDL-P grouping. A respective HDL-P subclass concentration is typically the sum of the particle concentrations of the respective subpopulation of its HDL-subclass, e.g., small HDL-P can include most or all of subclasses 1-8, medium can include most or all of 9-15, and large can include most or all of 16-26.

FIG. 1 illustrates a distribution of HDL-P grouped into 26 different subpopulations or subclasses, or into 8 different subpopulations or subclasses. The estimated diameters of the 26 different subpopulations or components (1-26) are shown in Table 1.

TABLE 1

Estimated diameters of 26 HDL subclasses as measured by NMR analysis

| HDL subclass | Estimated diameter (nm) |
|---|---|
| 26 | 13.5 |
| 25 | 13.0 |
| 24 | 12.5 |
| 23 | 12.0 |
| 22 | 11.5 |
| 21 | 11.0 |
| 20 | 10.8 |
| 19 | 10.6 |
| 18 | 10.5 |
| 17 | 10.0 |
| 16 | 9.7 |
| 15 | 9.4 |
| 14 | 9.2 |
| 13 | 9.0 |
| 12 | 8.6 |
| 11 | 8.5 |
| 10 | 8.4 |
| 9 | 8.3 |
| 8 | 8.2 |
| 7 | 8.1 |
| 6 | 8.0 |
| 5 | 7.9 |
| 4 | 7.8 |
| 3 | 7.6 |
| 2 | 7.5 |
| 1 | 7.4 |

The HDL subclasses of different size can be quantified from the amplitudes of their spectroscopically-distinct lipid methyl group NMR signals. See, Jeyarajah et al., Lipoprotein particle analysis by nuclear magnetic resonance spectroscopy, *Clin Lab Med.* (2006) 26: 847-870, the contents of which are hereby incorporated by reference as if recited in full herein. NMR spectroscopy has been used to concurrently measure very low density lipoprotein (VLDL), low density lipoproteins (LDL) and high density lipoproteins (HDL) as VLDL, LDL and HDL particle subclasses from in vitro blood plasma or serum samples. See, U.S. Pat. Nos. 4,933,844 and 6,617,167, the contents of which are hereby incorporated by reference as if recited in full herein. Generally stated, to evaluate the lipoproteins in a blood plasma and/or serum sample, the amplitudes of a plurality of NMR spectroscopy derived signals within a chemical shift region of the NMR spectrum can optionally be derived by deconvolution of the composite methyl signal envelope or spectrum to yield subclass concentrations.

The at least one inflammatory biomarker can include acute phase proteins that rise or fall in response to acute and chronic stimuli. See, e.g., Gabay et al., Acute-phase proteins and other systemic responses to inflammation, *N Engl J Med* (1999) 340: 448-454; Gornik et al., Glycosylation of serum proteins in inflammatory diseases, *Disease Markers* (2008) 25:267-278, the contents of which are hereby incorporated by reference as if recited in full herein. Inflammatory biomarkers can include, for example, GlycA, CRP (C-reactive protein), high-sensitivity (hs)-CRP, IL-6, fibrinogen, white blood cell count and the like. Further potential inflammatory biomarkers that may be used include one or more of the inflammatory biomarkers noted below. See, e.g., Myers et al., National Academy of Clinical Biochemistry Laboratory Medicine Practice Guidelines: Emerging Biomarkers for Primary Prevention of Cardiovascular Disease, *Clin Chem* (2009) 55: 2, pp. 378-384, the contents of which are hereby incorporated by reference as if recited in full herein. However, other inflammatory biomarkers may be used and measured by any suitable means.

Markers of Inflammation

Cytokines/Inflammation

Serum amyloid A
Sedimentation rate
Interleukin-6
Interleukin-8
Interleukin-18
Tumor necrosis alpha receptors 1 and 2
Tumor necrosis alpha
Viscosity
hsCRP Leukocytes/Platelets/Endothelium Intercellular adhesion molecule-1 (ICAM-1)
Vascular cell adhesion molecule-1 (VCAM-1)
P-selectin
E-selectin
Myeloperoxidase (MPO)
Lipoprotein associated phospholipase A2 (Lp-PLA2)
Monocyte chemoattractant protein-1
CD40 Ligand
White blood cell count Coagulation/Fibrinolysis Factor VIII
Von Willebrand factor
Plasminogen activator inhibitor-1
Tissue plasminogen activator
D-dimer
Fibrinogen The term "GlycA" refers to an inflammatory biomarker that is derived from a measure of composite NMR signal from carbohydrate portions of acute phase reactant glycoproteins containing N-acetylglucosamine and/or N-acetylgalactosamine moieties, more particularly from the protons of the 2-NAcGlc and 2-NAcGal methyl groups. GlycA is believed to be an aggregate primarily attributed to α1-acid glycoprotein, haptoglobin, α1-antitrypsin, α1-antichymotrypsin, and transferrin. See, Otvos J D, et al., GlycA: A composite nuclear magnetic resonance bio marker of systemic inflammation, *Clin Chem* (2015) 61(5):714-23, the contents of which are hereby incorporated by reference as if recited in full herein. The GlycA signal is centered at about 2.00 ppm in a plasma NMR spectrum at about 47 degrees C. (+/−0.5 degrees C.). The peak location is independent of spectrometer field but may vary depending on analysis temperature of the biosample and is not found in urine biosamples. Thus, the GlycA peak region may vary if the temperature of the test sample varies. The GlycA NMR signal may include a subset of NMR signal at the defined peak region so as to include only clinically relevant signal contributions and may exclude a protein contribution to the signal in this region as will be discussed further below. See, U.S. Patent Application Publication 2013/0328561 for a description of GlycA and methods of calculating same, the contents of which are hereby incorporated by reference as if recited in full herein.

It is also noted that while NMR measurements of the lipoprotein particles and inflammatory biomarker(s) are contemplated as being particularly suitable for NMR analyses it is also contemplated that other technologies may be used to measure these parameters, now or in the future and embodiments of the invention are not limited to this measurement methodology.

Also, although primarily described with respect to deconvolution NMR methods, other NMR methods may also be used including different deconvolving protocols or other NMR based protocols in lieu of the deconvolving protocol described herein. See, e.g., Kaess et al., The lipoprotein subfraction profile: heritability and identification of quantitative trait loci, J Lipid Res. Vol. 49 pp. 715-723 (2008); and Suna et al., 1H NMR metabolomics of plasma lipoprotein subclasses: elucidation of metabolic clustering by self-organising maps, NMR Biomed. 2007; 20: 658-672. Examples of non-NMR methods include, for example, flotation and ultracentrifugation employ a density-based separation technique for evaluating lipoprotein particles. Ion mobility analysis is a different technology for measuring lipoprotein subclasses. Different inflammatory biomarkers can be measured using suitable analysis techniques that do not require NMR, for example.

B. An HDL-Inflammatory Biomarker Interaction Parameter Improves CVD Prediction

HDL-P alone is not always anti-atherogenic. Thus, as discussed above the HDL and inflammation risk parameter $(HxI)_{CVD}$ together may be able to stratify risk for subjects that are not readily identifiable using HDL-P measurement alone.

The new interaction parameter described herein includes at least one HDL biomarker and at least one inflammatory biomarker. Such an interaction parameter may be used for improved assessments of CVD risk.

A new HDL and inflammatory biomarker risk parameter $((HxI)_{CVD})$ may be used for assessing CVD risk, and/or for one or more of drug discovery, clinical trials, selecting the most appropriate therapy individualized to the patient, monitoring a response to a therapy or therapies and the like.

The $(HxI)_{CVD}$ risk parameter can include at least one HDL-subclass parameter multiplied by a defined biomarker inflammatory marker.

The $(HxI)_{CVD}$ risk parameter can include, as the interaction parameter, a measurement of GlycA multiplied by a concentration of a defined subpopulation of high density lipoprotein particles (HDL-P). The $(HxI)_{CVD}$ risk parameter can additionally or alternatively include an interaction parameter of GlycA multiplied by the concentration of a second (different) defined subpopulation of HDL-P.

For example, a risk parameter may be calculated by the following equations:

$$(HxI)_{CVD} = c_1(cH1) + c_2(INFLAM) + c_3(INTER_{H1}); \text{ or}$$

$$(HxI)_{CVD} = c_4(cH8) + c_5(INFLAM) + c_6(INTER_{H8})$$

wherein INFLAM is the concentration of the at least one inflammatory biomarker, $INTER_{H1} = INFLAM*cH1$, $INTER_{H8} = INFLAM*cH8$, and wherein "$c_1$-$c_6$" represent respective defined coefficients from a mathematical model of CVD events in a study population for the associated risk parameter.

Surprisingly, the inventors have found that the use of a new "composite" HDL and inflammation risk parameter ("$(HxI)_{CVD}$") that includes at least one HDL and inflammation interaction parameter can statistically improve CVD risk prediction models and may be useful to stratify different CVD risk for patients and/or to provide a therapy tool that may more accurately reflect efficacy and/or non-efficacy of a therapy for reducing or changing CVD risk. The term "interaction parameter" refers to at least two different defined parameters which are combined (multiplied) as a product and/or ratio. Interaction is also referred to as "effect modification," since one variable affects the relation of a second variable with an outcome such as CVD. The at least one HDL and at least one inflammation interaction parameter may include a defined HDL-P parameter and at least one defined inflammatory biomarker parameter that are mathematically combined as a product or and/or ratio. The term "composite" with respect to $(HxI)_{CVD}$ means that a plurality of different defined parameters are mathematically combined (added or subtracted) to the at least one HDL and inflammation interaction parameter.

Examples of interaction parameters include, but are not limited to, a concentration of an HDL-P subpopulation multiplied by a concentration measurement of one or more inflammatory biomarkers. Additionally, or alternatively, exemplary parameters may include a sum of two or more HDL-P subclass concentrations multiplied by a concentration of one or more inflammatory biomarkers (typically summed if more than one inflammatory biomarker is used). Or individual HDL-P subclass concentrations may be used to generate an interaction parameter. If two or more HDL-P and inflammation interaction parameters are used, the same inflammatory biomarker can be used for each, or different inflammatory biomarkers may be used for each interaction parameter.

In some embodiments, the $(HxI)_{CVD}$ risk parameter comprises at least two (and in some embodiments, only two) interaction parameters using the same inflammatory biomarker. The inflammatory biomarker can be a single biomarker or may be a plurality and, if so, the different biomarker concentrations may be summed for use in the $(HxI)_{CVD}$ risk parameter. In some embodiments, the $(HxI)_{CVD}$ risk parameter comprises two HDL-P and inflammatory interaction parameters and each interaction parameter can include the same inflammatory biomarker.

By way of example, $(HxI)_{CVD}$ typically comprises at least one HDL subclass and at least one inflammation marker, e.g., (H1xGlycA) or (H8xGlycA). Multiple parameters may be summed (or subtracted if the model coefficient is negative—illustrating a negative correlation, for example).

Thus $(HxI)_{CVD}$ can include a particular subclass of HDL-P, such as "H1" or "H8," as described in part C, herein below. The $(HxI)_{CVD}$ risk parameter can also include the (concentration) measurement of the at least one inflammatory biomarker which may be unitless (for example, if measured by NMR) or provided in concentration units (if a concentration factor is applied to the NMR measurement or if a different measurement technique is used).

$(HxI)_{CVD}$ can also include other discrete HDL-P subclass components, typically adjusted by respective defined coefficients from a mathematical model of CVD risk from a study population. $(HxI)_{CVD}$ can include, for example, one or more of H1, H8, HLP, and/or HMSP, e.g.

Figure 2:
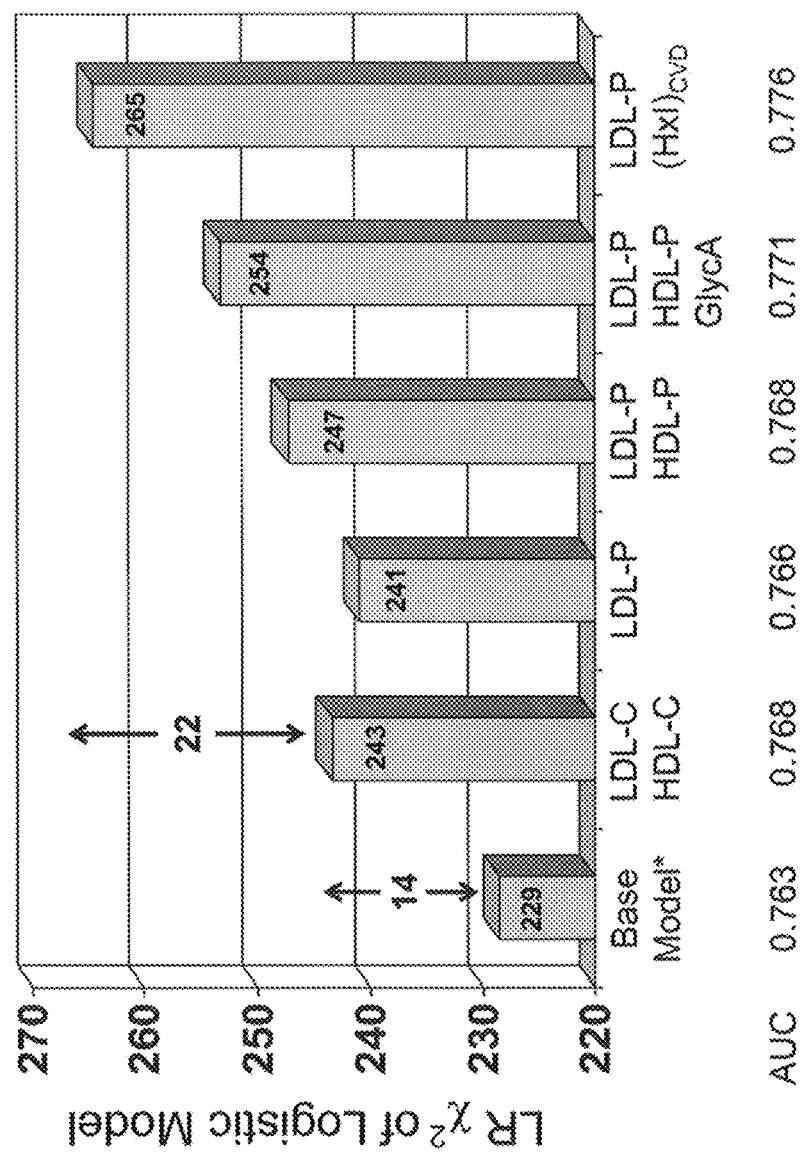
FIG. 2 is a graph illustrating CVD risk associations (as indicated by the model's likelihood ratio (LR) $\chi 2$ statistic for each of six different logistic regression models (all models have the same parameters as the base logistic regression model for incident CVD events in MESA (n=274/5534), adjusted for age, sex, race, smoking, SBP, hypertension medication, BMI, diabetes, BMI, and triglycerides) showing the increased $\chi 2$ with the $(HxI)_{CVD}$ risk parameter included in the model according to embodiments of the present invention.

FIG. 2 illustrates model $\chi^2$ values for different prediction models which differ according to which variables are added to the "base" logistic regression model for incident CVD events in MESA (n=274/5534), which includes age, sex/gender, race, SBP, hypertension medication use, smoking, diabetes, BMI and triglycerides. The increase in model $\chi^2$ when using both LDL-P and $(HxI)_{CVD}$ is 22 points above "standard" or conventional risk assessments using LDL-C and HDL-C. The AUC value also illustrates this improvement (AUC of 0.776 versus 0.768). It can be seen that the increase provided by $(HxI)_{CVD}$ is better than when LDL-P, HDL-P and the inflammatory biomarker (GlycA) parameters are considered separately (FIG. 2).

Figure 3:
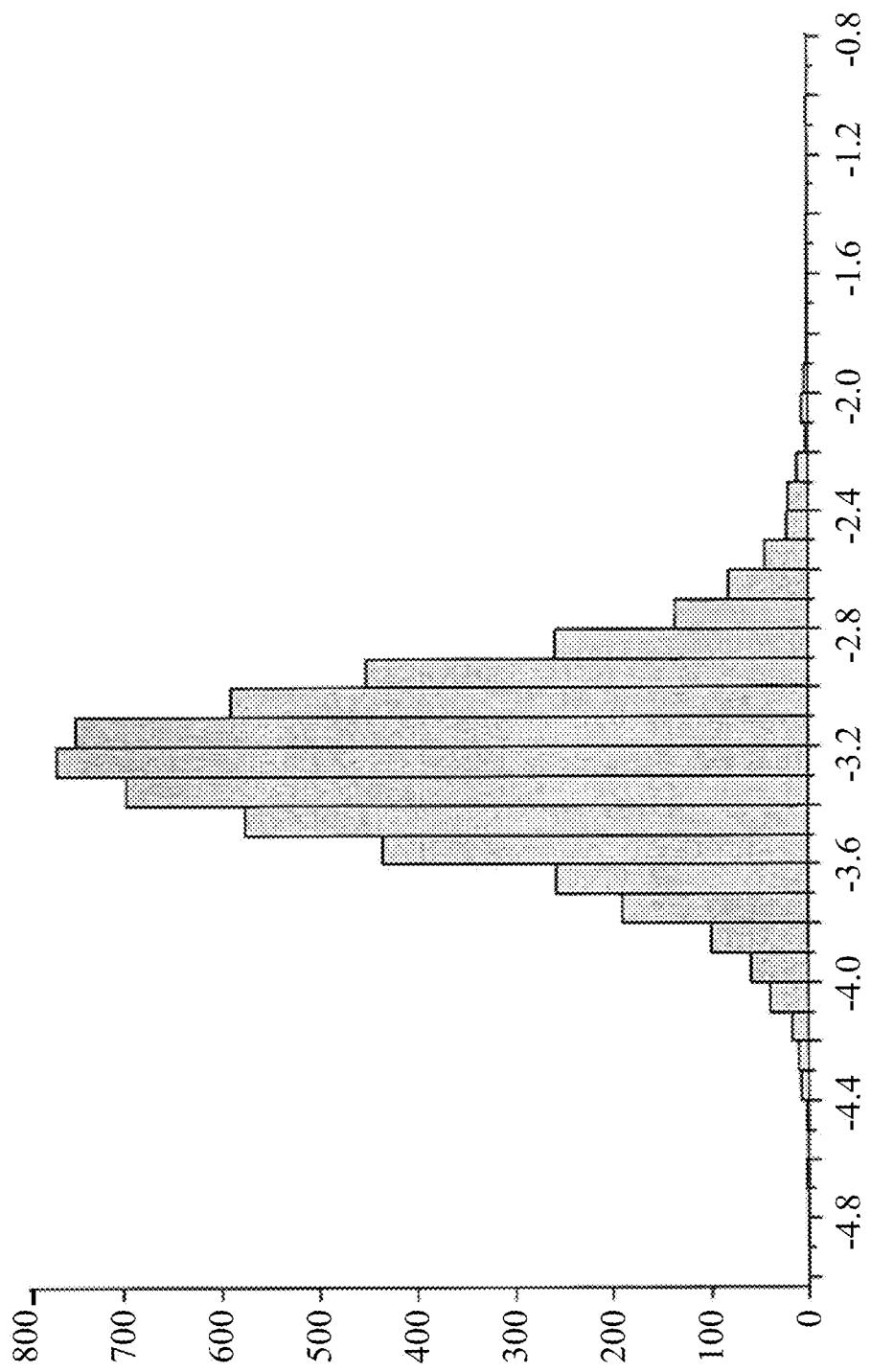
FIG. 3 is a graph of a distribution of $(HxI)_{CVD}$ values (unitless) in the MESA study population (n=5542) based on embodiments of the present invention.

FIG. 3 illustrates the distribution of $(HxI)_{CVD}$ in MESA participants (n=5542), illustrating a bell-shaped distribution ranging between about −4.85 and about −0.718, with a mean of about −3.256 and a standard deviation of about 0.322. Notably, the distribution is normal, or not skewed, indicating that the marker distribution is nearly normal like that of cholesterol or other CVD biomarkers.

FIG. 4 is a chart that illustrates an example where five NMR-derived HDL and inflammation parameters are combined to generate $(HxI)_{CVD}$ according to some particular embodiments of the present invention. These include HLP (HDL-P of approximately 10.0-13.5 nm diameter) and HMSP (HDL-P of approximately 7.4-9.7 nm diameter), GlycA, and the interaction terms HLP*GlycA and HMSP*GlycA. When combined, the statistical relevance improves relative to the use of these parameters individually as indicated.

The different coefficients ("c"), or weightings, for the composite calculation for each of the constituents can be defined by the logistic regression model (but other mathematical models may be used as well as other study populations as noted above). Equations 1-3 are examples with each coefficient identified below as using the same coefficient letter with a numerical subscript. Thus, the "c" coefficient can represent different values for each parameter. Three exemplary equations are shown below which employ two interaction parameters (INTERA and INTERB) and can be used to calculate the new risk parameter according to some embodiments. The second equation illustrates that INTERA is GlycA*HLP and INTERB is GlycA*HMSP, as the two interaction parameters. Thus, the first equation is presented in more generic form which acknowledges that other interaction parameters may be used, particularly using other Inflammatory biomarkers (which is shown in Equations 1 and 3 by the term ("INFLAMB")). The third equation is the first equation, but states the coefficient with a respective negative or positive sign of the coefficient so that the number "c" from a model is inserted into the equation as a positive number (as an associated negative sign is already in this version of the equation). The second equation also provides the polarity of the sign (negative or positive) of each respective coefficient. Equations 2 and 3 are provided in this form to illustrate the negative and positive correlations of the noted parameter according to embodiments of the invention.

$$(HxI)_{CVD} = c_1 HLP + (c_2 HMSP) + (c_3 INFLAMB) + (c_4 INTERA) + c_5 INTERB \quad \text{Equation (1)}$$

$$(HxI)_{CVD} = c_1 HLP + (-c_2 HMSP) + (-c_3 GlycA) + (-c_4 HLPxGlycA) + c_5 HMSPxGlycA \quad \text{Equation (2)}$$

$$(HxI)_{CVD} = c_1 HLP + (-c_2 HMSP) + (-c_3 INFLAMB) + (-c_4 INTERA) + c_5 INTERB \quad \text{Equation (3)}$$

In the example shown in FIG. 5, using the noted MESA study population and the exemplary inflammatory biomarker GlycA, the coefficients are shown below in Table 2. However, it is also noted that other inflammatory biomarkers and other HDL interaction parameters may be used and/or or only a single HDL and inflammatory biomarker interaction parameter may be used, and the exemplary coefficients and equations discussed are by way of example only.

TABLE 2

| Parameter | | Coefficient value "c" |
|---|---|---|
| HLP | $c_1$ | 0.2328 |
| HMSP | $c_2$ | −0.2024 |
| INFLAMB | $c_3$ | −0.0063 |
| INTERA | $c_4$ | −0.00079 |
| INTERB | $c_5$ | 0.000499 |

FIG. 5 is a chart listing the parameter estimates for the variables, including $(HxI)_{CVD}$ shown in FIG. 4, in a logistic regression risk prediction model for CVD events (n=274) in MESA participants (n=5534) during five years of follow up. $(HxI)_{CVD}$ is shown by the Wald Chi-square ($\chi^2$) statistic to be associated with CVD risk at least as strongly as the major established CVD risk factors, e.g., age, gender, SBP, smoking, and diabetes.

Figure 6:
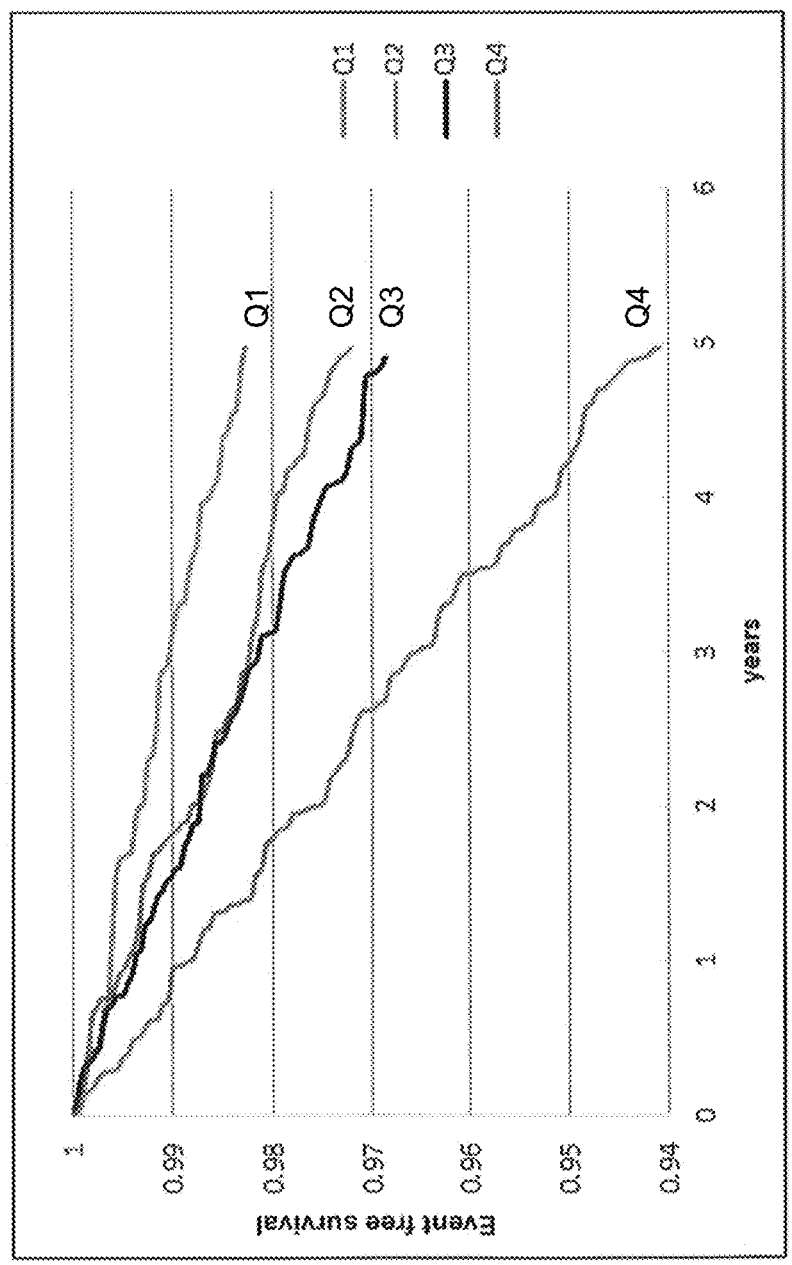
FIG. 6 is a graph showing event-free survival during 5 years of follow-up for 4 subgroups divided by $(HxI)_{CVD}$ quartile (subjects divided into quartiles by the $(HxI)_{CVD}$ shown in FIG. 4) from Cox proportional hazards analysis for incident CVD events in MESA (n=274/5534), adjusted for age, sex/gender, race, smoking, BMI, diabetes, SBP, hypertension medication use, and LDL-P according to embodiments of the present invention.

FIG. 6 is a graph showing event free survival during 5 years of follow-up for 4 subgroups in MESA. Subjects were categorized in quartiles ("Q") by the $(HxI)_{CVD}$ shown in FIG. 4, from Cox proportional hazards analysis for incident CVD events in MESA (n=274/5534), adjusted for age, sex/gender, race, smoking, BMI, diabetes, SBP, hypertension medication use, and LDL-P, according to embodiments of the present invention. Those with $(HxI)_{CVD}$ in the highest quartile (Q4) have significantly increased risk relative to those in the 3 lower quartiles.

Figure 7A:
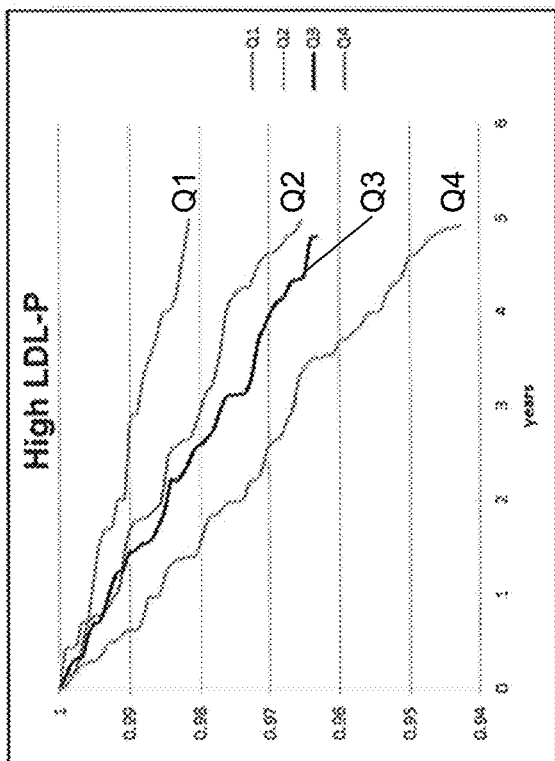
FIGS. 7A and 7B are graphs showing event free survival in MESA by quartile of $(HxI)_{CVD}$ for low and high levels of LDL-P, respectively, again from Cox proportional hazards analysis for incident CVD events in MESA (n=274/5534), adjusted for age, sex/gender, race, smoking, BMI, diabetes, SBP, hypertension medication use, and triglycerides. Low and high LDL-P values are below and above the median (1265 nmol/L), respectively, according to embodiments of the present invention.
Figure 7B:
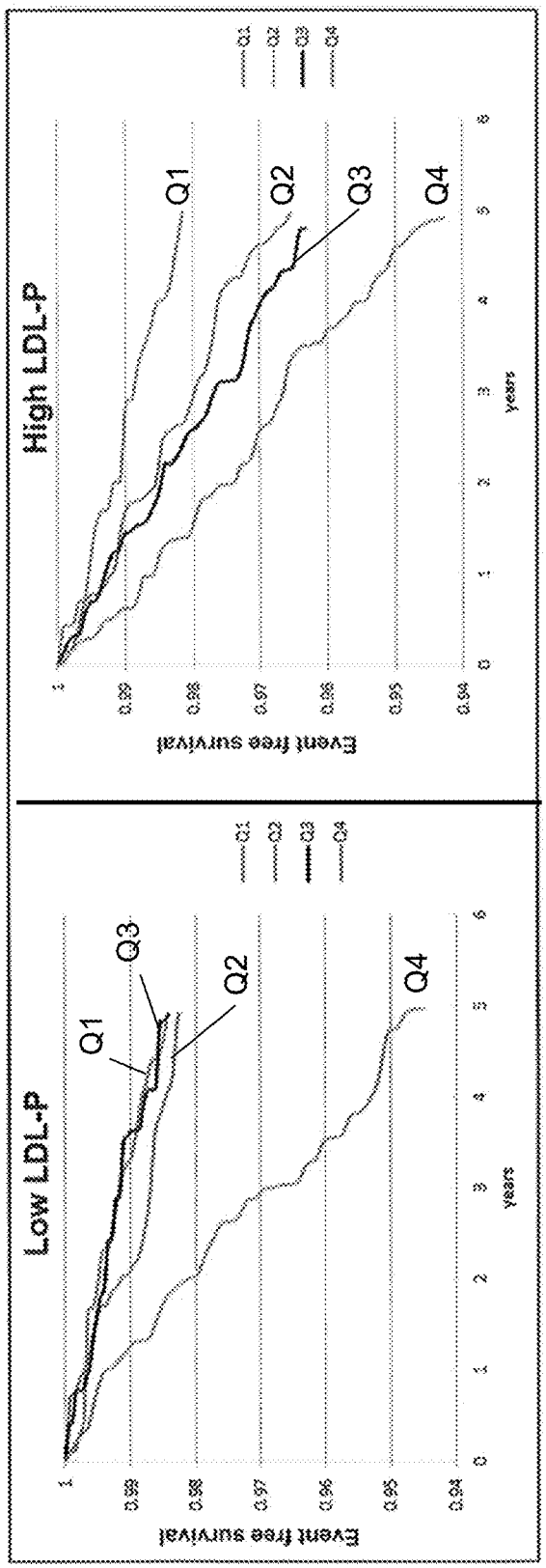

FIGS. 7A and 7B are graphs showing event free survival in MESA by quartile ("Q") of $(HxI)_{CVD}$ for low and high levels of LDL-P, respectively, again from Cox proportional hazards analysis for incident CVD events in MESA (n=274/5534), adjusted for age, sex/gender, race, smoking, BMI, diabetes, SBP, hypertension medication use, and triglycerides. Low and high LDL-P values are below and above the median (1265 nmol/L), respectively, according to embodiments of the present invention. Those with low LDL-P and high $(HxI)_{CVD}$ (Q4) have significantly increased risk relative to persons with low LDL-P and Q1-Q3 $(HxI)_{CVD}$. High LDL-P indicates increased risk for all values of $(HxI)_{CVD}$ but Q1 $(HxI)_{CVD}$ and high LDL-P show less relative risk.

Figure 8:
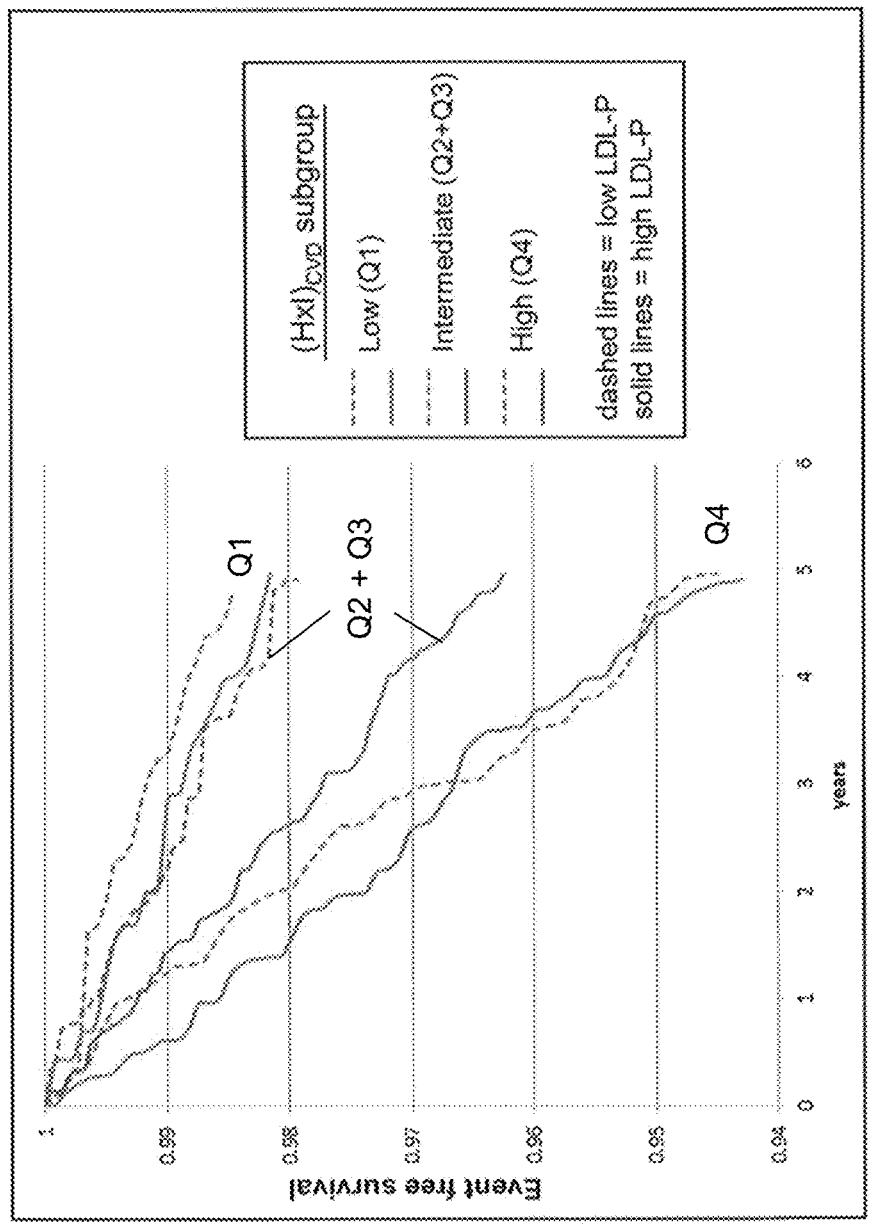
FIG. 8 is a graph of event free survival in MESA by LDL-P and $(HxI)_{CVD}$ subgroupings for low and high levels of LDL-P, again from Cox proportional hazards analysis for incident CVD events in MESA (n=274/5534), adjusted for age, sex/gender, race, smoking, BMI, diabetes, SBP, hypertension medication use, and triglycerides. Low and high LDL-P values are below and above the median (1265 nmol/L), respectively, according to embodiments of the present invention.

FIG. 8 is a graph of event-free survival in MESA by LDL-P and $(HxI)_{CVD}$ subgroupings for low and high levels of LDL-P, again from Cox proportional hazards analysis for incident CVD events in MESA (n=274/5534), adjusted for age, sex/gender, race, smoking, BMI, diabetes, SBP, hypertension medication use, and triglycerides. Low and high LDL-P values are below and above the median (1265 nmol/L), respectively, according to embodiments of the present invention. This graph presents the information shown in FIGS. 7A and 7B by way of a more direct comparison of low LDL-P and high LDL-P and combines intermediate $(HxI)_{CVD}$ values (Q2 and Q3), thus illustrating three ranges of $(HxI)_{CVD}$, Q1, Q4 and Q2+Q3.

FIG. 9 is a chart illustrating logistic regression model parameters and associated statistical relevance values (and coefficients) used to calculate predicted probabilities of a CVD event when using one HDL and inflammation interaction parameter (HMSP*GlycA) and only small and medium HDL-P subclasses (a concentration of small and medium subclasses as a parameter) according to embodiments of the present invention.

Figure 10:
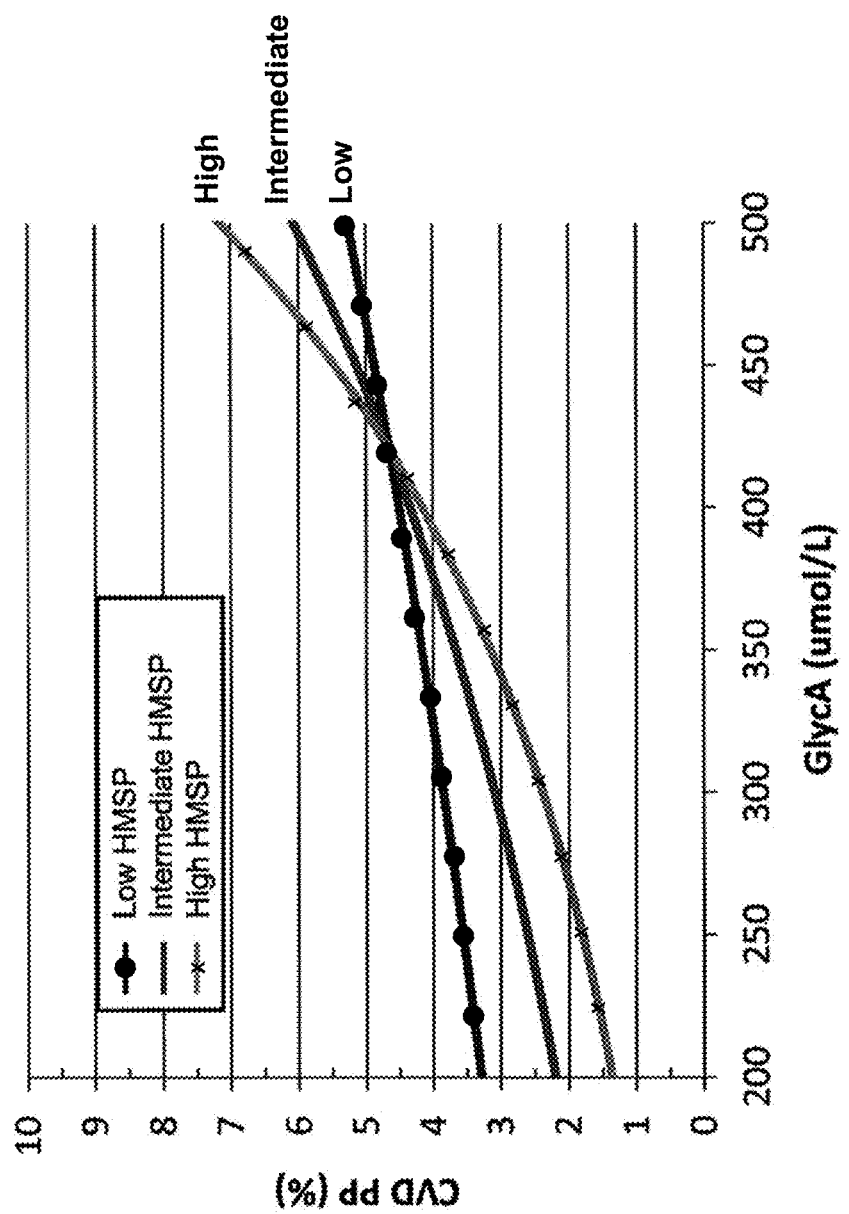
FIG. 10 is a graph illustrating CVD risk associated with low, intermediate and high values of the sum of small and medium HDL-P subclasses (HMSP) as a function of increasing levels of an inflammatory biomarker (as shown, GlycA) (percent of predicted probabilities for CVD events (CVD PP %) in MESA during a 5-year follow-up (n=274/5534) from logistic regression for a 60-year old non-smoking, non-diabetic Caucasian female taking hypertension medication with SBP=140 mm Hg, BMI=29 kg/m$^2$, LDL-P=1500 n/mol/L, triglycerides=150 mg/dL). Low, intermediate and high for this example, are 23.6, 27.6 and 32.3 μmol/L ($20^{th}$, $50^{th}$ and $80^{th}$ percentile), respectively, according to embodiments of the present invention.

FIG. 10 is a graph illustrating low, intermediate and high values of the sum of small and medium HDL-P subclasses ("HMSP") versus increasing levels of an inflammatory biomarker (as shown, GlycA) based on predicted probabilities for CVD events in MESA during a 5 year follow-up (n=274/5534) from logistic regression for a 60-year old non-smoking, non-diabetic Caucasian female taking hypertension medication with SBP=140 mm Hg, BMI=29 kg/m$^2$, LDL-P=1500 n/mol/L, triglycerides=150 mg/dL). Low, intermediate and high for this example, are 23.6, 27.6 and 32.3 µmol/L (20$^{th}$, 50$^{th}$ and 80$^{th}$ percentile), respectively, according to embodiments of the present invention. As shown, high values of HMSP go from a lower CVD percent probability relative to low and intermediate values at lower concentration ranges of the inflammatory biomarker but transition to the same risk at about 425 µmol/L, then actually be associated with increased risk above about 425 µmol/L relative to the low and intermediate concentrations of HMSP.

FIG. 11 is a chart illustrating logistic regression model parameters and associated statistical relevance values (and coefficients) used to calculate predicted probabilities of a CVD event (percent) when using one HDL and inflammation interaction parameter (HLP*GlycA) and a concentration of only large HDL-P subclasses (HLP) according to embodiments of the present invention.

Figure 12:
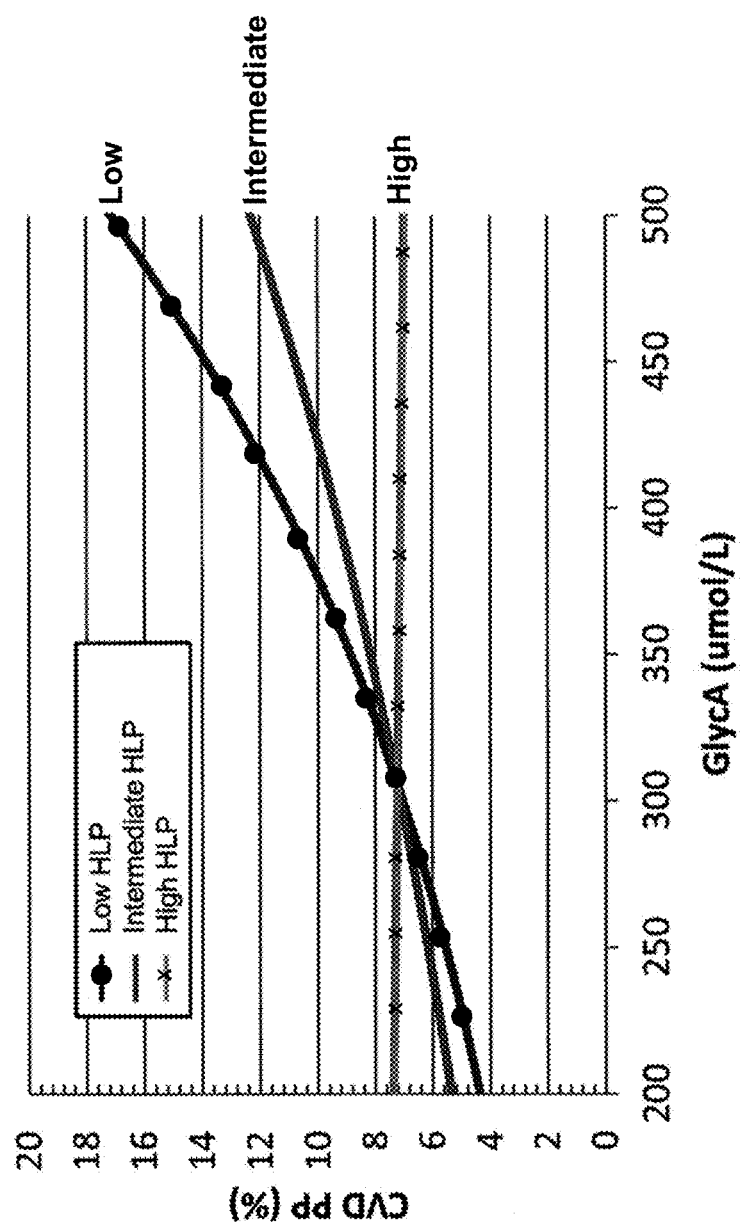
FIG. 12 is a graph illustrating CVD risk associated with low, intermediate and high values of the sum of large HDL-P subclasses (HLP) as a function of increasing levels of inflammatory biomarker GlycA (predicted probabilities for CVD events in MESA during a 5 year follow-up (n=274/5534) from logistic regression for a 60-year old non-smoking, non-diabetic Caucasian female taking hypertension medication with SBP=140 mm Hg, BMI=29 kg/m$^2$, LDL-P=1500 n/mol/L, triglycerides=150 mg/dL). Low, intermediate and high for this example, are 3.0, 5.1 and 8.5 μmol/L ($20^{th}$, $50^{th}$ and $80^{th}$ percentile), respectively, according to embodiments of the present invention.

FIG. 12 is a graph illustrating low, intermediate and high values of the sum of large HDL-P subclasses ("HLP," corresponding to subclasses 16-26 as shown in FIG. 1) versus increasing levels of an inflammatory biomarker (as shown, GlycA) (predicted probabilities for CVD events in MESA during a 5 year follow-up (n=274/5534) from logistic regression for a 60-year old non-smoking, non-diabetic Caucasian female taking hypertension medication with SBP=140 mm Hg, BMI=29 kg/m$^2$, LDL-P=1500 n/mol/L, triglycerides=150 mg/dL). Low, intermediate and high for this example, are 3.0, 5.1 and 8.5 µmol/L (20$^{th}$, 50$^{th}$ and 80$^{th}$ percentile), respectively, according to embodiments of the present invention. As shown, high HLP values correspond to a substantially constant percent probability over the range of the inflammatory biomarker shown while low and intermediate values show increased risk as the concentration of the inflammatory biomarker increases above about 300 µmol/L.

The mathematical models to assess CVD risk can comprise other clinical statistically relevant parameters such as, for example, one or more of gender, age, systolic blood pressure, smoking and whether on hypertension medicine and the like. Optionally, race, type 2 diabetes, BMI and triglycerides or other parameters may also be included.

It is known that different therapies that increase HDL-C by the same amount may not increase the HDL subclasses proportionately. Some drugs, for example, increase HDL-C mainly by increasing the number of small HDL particles (such as those in the fibrate class). Others increase mainly large HDL-P. The HDL particle subclass concentrations can change differentially with different therapies, indicating potentially greater or lesser clinical benefit and may provide enhanced protocols for evaluating therapeutic efficacy. See, e.g., Rashedi N, Brennan D, Kastelein J J, Nissen S E, Nicholls S. 2011 *European Atherosclerosis Society meeting presentation*. It is contemplated that (HxI)$_{CVD}$ risk parameter can be used to evaluate a therapy and/or clinical benefit, alone or in combination with other parameters, particularly over time or in response to a change in an administered drug, for example.

The (HxI)$_{CVD}$ risk parameter may provide more reliable data on therapies, clinical trials and the like about the potential performance of drugs aimed at reducing CVD and/or CHD. That is, instead of merely determining whether a drug can increase HDL-C, it may be desirable to evaluate whether the drug decreases a particular (HxI)$_{CVD}$ risk parameter, potentially also with any change to LDL-P, e.g., from a high to low concentration.

Thus as shown herein, an (HxI)$_{CVD}$ risk parameter, which comprises an HDL-inflammation interaction parameter, may provide actionable information. That is, the (HxI)$_{CVD}$ risk parameter may be provided to a subject or their healthcare provider in a report, such that the subject may modify his or her diet, exercise, smoking, or other behaviors, based at least in part on the calculated (HxI) CVD. Alternatively or additionally, a healthcare provider may prescribe, recommend, or decide upon a treatment or therapy for the subject, or a change in treatment or therapy, based at least in part on the calculated (HxI)$_{CVD}$. As such, the (HxI)$_{CVD}$ risk parameter or multimarker may be monitored over time (i.e., by taking one or more subsequent biosamples) to allow the subject or their healthcare provider to determine whether the (HxI)$_{CVD}$ risk parameter or multimarker has increased or decreased as a result of a therapy, treatment, or behavior modification.

C. Analysis of Fewer HDL-P Subclasses Improves CVD Prediction

Because analysis of a larger number of lipoprotein subclasses may generate greater measurement imprecision overall, alternative embodiments may utilize a smaller number of HDL subclasses, so as to reduce this imprecision. For example, the deconvolution model may be adjusted to analyze HDL particles as divided into 8 different subclasses by particle size, rather than 26 different subclasses as demonstrated above, as shown in FIG. 1. The reduced number of subclasses can increase precision. For example, in certain embodiments H1 may represent a diameter range of about 7.0-7.6 nm, and H8 may represent a diameter range of about 11.5-13.5 nm.

Figure 13:
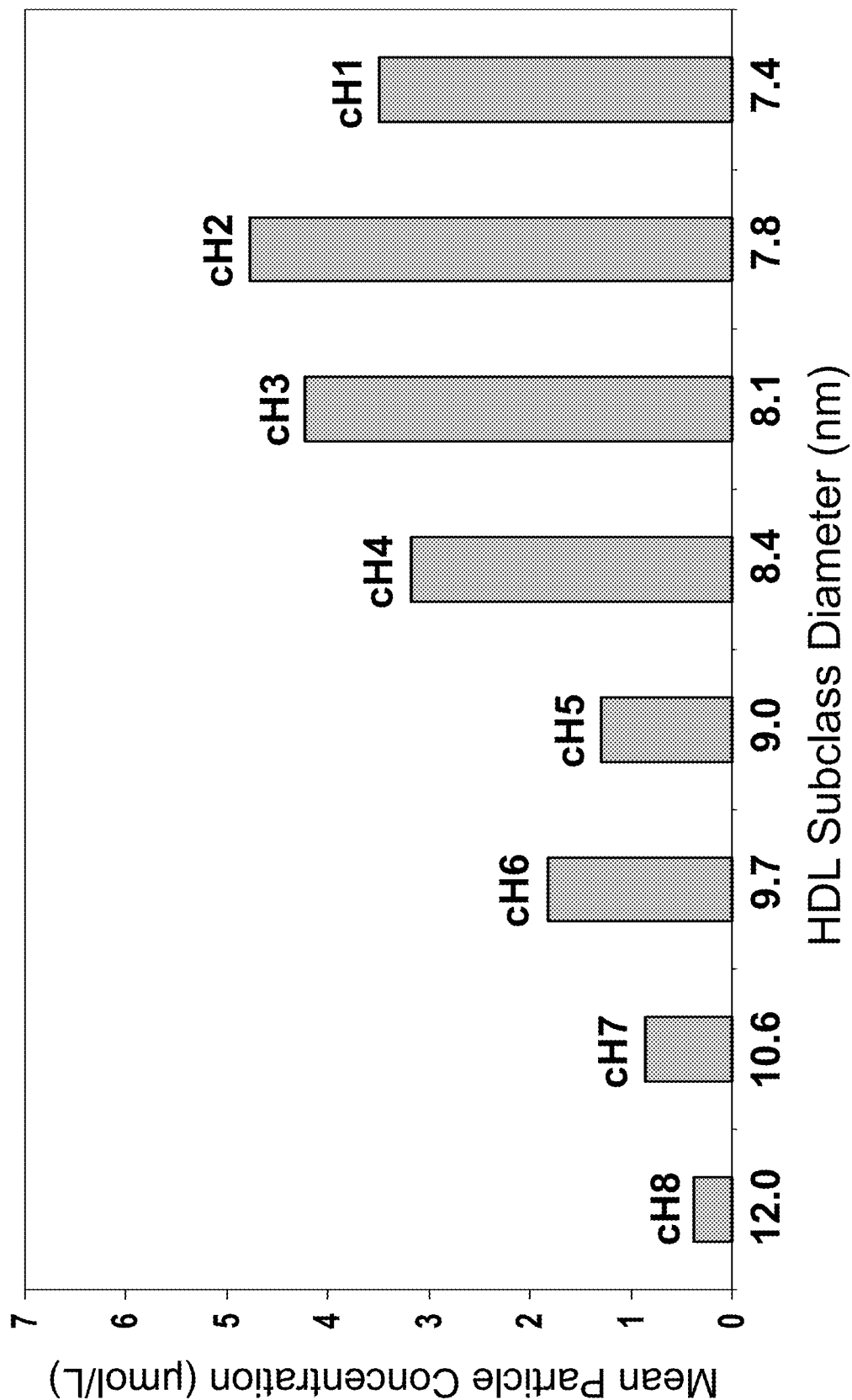
FIG. 13 is a graph of mean concentrations (μmol/L) of HDL-P grouped into 8 subpopulations (sizes of H1-H8), rather than 26 subpopulations, in healthy subjects (n=5532).

In the embodiment shown in FIG. 13, the different subpopulations of HDL-P can be identified by a number from H1-H8, with "H1" representing the smallest size HDL subpopulation (diameter average 7.4 nm) and "H8" being the largest size HDL subpopulation (diameter average 12.0 nm). FIG. 13 shows a distribution of concentrations of 8 different subpopulations of HDL-P in a healthy cohort of Dutch individuals (n=5532). The small 'c' before each subclass (i.e., cH1-cH8) refers to the fact that mean particle concentrations shown here are calibrated to account for substantial discrepancies between lipoprotein analysis methodologies, as reported by Hutchins, et al. *Clin. Chem.* (2014) 60: 1393-401, the contents of which are hereby incorporated by reference as if recited in full herein. When the development of NMR-based lipoprotein concentration measurements was in infancy, no other measurement method was available by which to calibrate the NMR-derived concentrations. As a result, the NMR-derived HDL-P concentrations previously reported were likely about 50% higher than the actual absolute concentrations. Thus the present calibration is a step toward harmonization between lipoprotein measurement methodologies.

Estimated diameters for the 8 different HDL subpopulations or components (H1-H8) are shown in Table 3, with the approximate corresponding subclasses from the 26 subclass analysis of FIG. 1. The small "c" before each term (e.g., "cH1") represents a coefficient from a mathematical model of CVD events in a study population for the associated risk parameter, as described herein.

Surprisingly, when HDL particles are analyzed in 8 subclasses as shown in Table 3, utilizing the largest diameter (H8) and smallest diameter (H1) subclasses to generate the HDL and inflammation risk parameter (HxI)$_{CVD}$ may allow improved risk stratification for subjects that were not previously distinguishable, using HDL information with inflammatory status. The average particle diameters reported in the table are approximate and may be more accurately represented by a diameter range for each subclass (e.g., H1 may be about 7.0-7.6 nm, and H8 may be about 11.5-13.5 nm).

TABLE 3

Estimated diameters of 8 HDL subclasses as measured by NMR analysis

| HDL subclass | Estimated diameter (nm) | Corresponding Subclasses 1-26 | Alternative Subclasses |
|---|---|---|---|
| cH8 | 12.0 | 22-26 | Large HLP |
| cH7 | 10.6 | 17-21 | |
| cH6 | 9.7 | 15-16 | Medium HMSP |
| cH5 | 9.0 | 12-14 | |
| cH4 | 8.4 | 9-11 | |
| cH3 | 8.1 | 6-8 | Small |
| cH2 | 7.8 | 4-5 | |
| cH1 | 7.4 | 1-3 | |

FIG. 14 is a chart that illustrates an example where an NMR-derived HDL parameter for the largest HDL-P subclass, designated H8 according to Table 3, is combined with the NMR-derived inflammation parameter, GlycA, to generate the $(H8xI)_{CVD}$ multimarker according to some particular embodiments of the present invention. The data is based on a logistic regression model for incident CVD events in MESA participants (n=5660) during 9 years of follow-up. The equation includes the numerical addition of 5 to the $(H8xI)_{CVD}$ multimarker to ensure that all values are positive.

FIG. 15 is a chart that illustrates an example where an NMR-derived HDL parameter for the smallest HDL-P subclass, designated H1 according to Table 3, is combined with the NMR-derived GlycA inflammation parameter to generate the $(H1xI)_{CVD}$ multimarker according to some particular embodiments of the present invention. The data is based on a logistic regression model for incident CVD events in MESA participants (n=5660) during 9 years of follow-up. The equation includes addition of 5 to the $(H1xI)_{CVD}$ multimarker to ensure that all values are positive.

FIG. 16 is a chart that illustrates an example where three NMR-derived HDL and inflammation parameters are combined to generate the composite $(HxI)_{CVD}$ multimarker according to some particular embodiments of the present invention. These include the (H1*GlycA) and (H8*GlycA) multimarkers as well as H2-7 combined, as shown in the equation below the chart. When combined, the statistical relevance improves relative to the use of these parameters individually.

Figure 17:
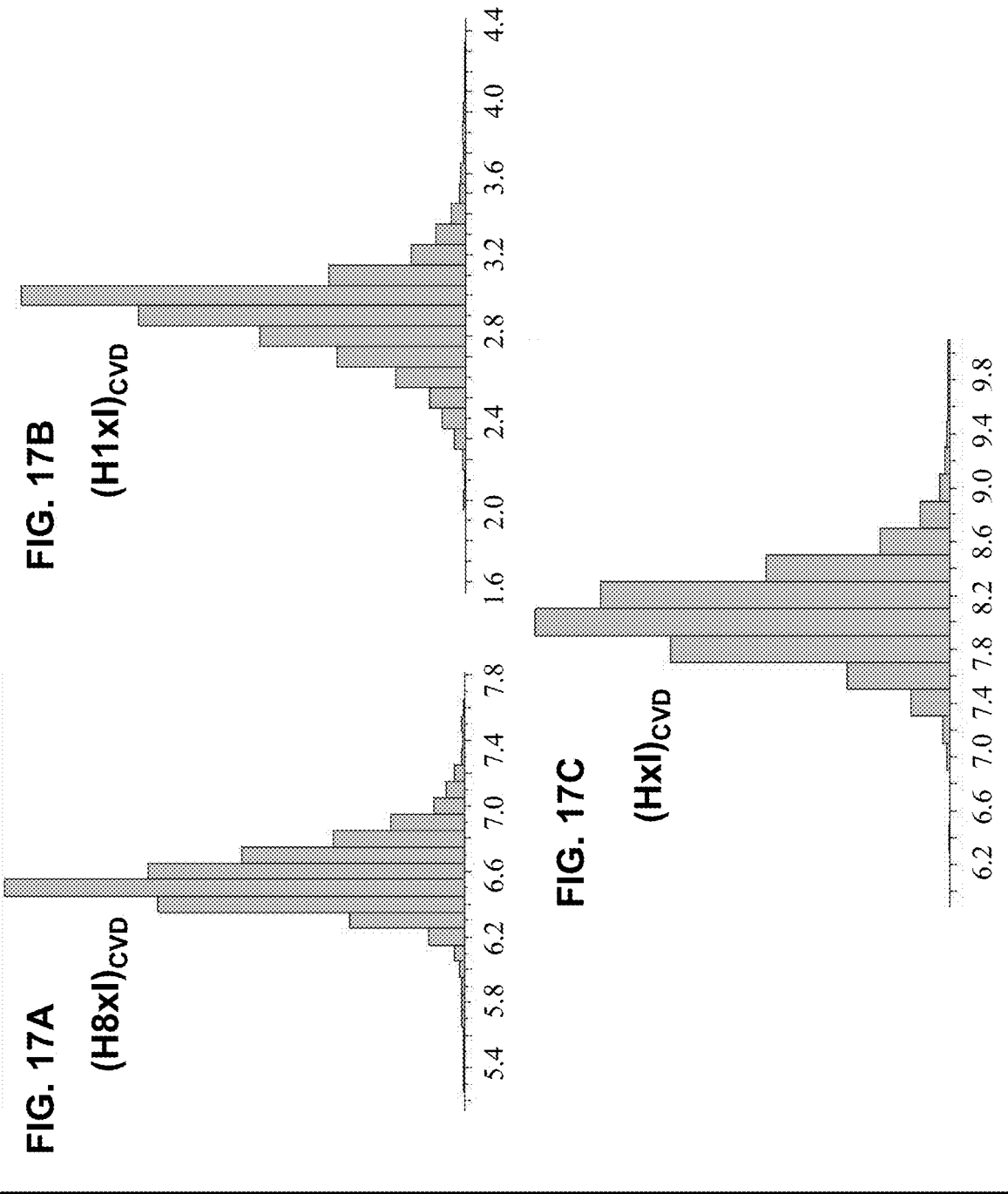
FIGS. 17A, 17B, and 17C show graphical distributions of $(H8xI)_{CVD}$, $(H1xI)_{CVD}$, and $(HxI)_{CVD}$ values (unitless), respectively, in the MESA study population (n=5682) based on embodiments of the present invention.

FIGS. 17A, 17B, and 17C illustrate the distributions of the calculated multimarker parameters in MESA participants (n=5682), illustrating a nearly bell-shaped distribution for each. Panel A shows $(H8xI)_{CVD}$, Panel B shows $(H1xI)_{CVD}$, and Panel C shows $(HxI)_{CVD}$, where (HxI) is calculated as shown in FIG. 16. Notably, the distribution is not markedly skewed, indicating that the marker is normally distributed like cholesterol and other CVD biomarkers.

FIG. 18 shows model $\chi^2$ values for each of eleven different prediction models which differ according to which variables are added to the "base" logistic regression model for incident CVD events in MESA (n=458/5660), which includes age, sex/gender, race, hypertension, smoking, diabetes, BMI and VLDL-P. The increase in model $\chi^2$ when using LDL-P and $(HxI)_{CVD}$ (e.g., for model 11) or LDL-P, $(H8xI)_{CVD}$, $(H1xI)_{CVD}$, and H2-7 (e.g., for model 10) is about 36 points above "standard" or conventional risk assessments using LDL-C and HDL-C. This corresponds to improved prediction (i.e., improved risk evaluation) for models 10 and 11.

As suggested by FIGS. 10 and 12, the effect of having a high level of any particular subclass of HDL-P may be at least partially dependent on co-existing inflammatory status. That is, inflammation may modulate HDL functionality.

Figure 19:
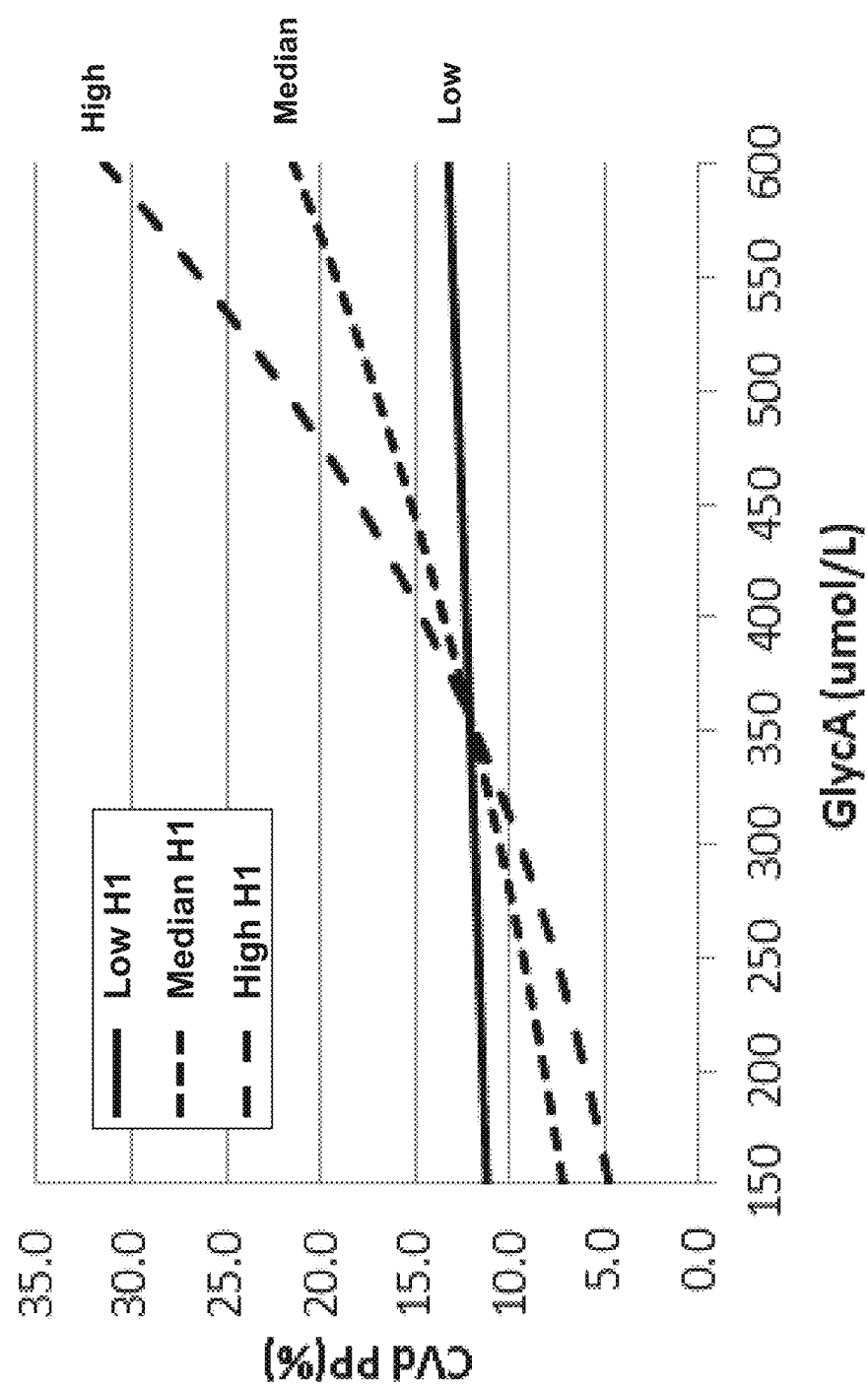
FIG. 19 is a graph illustrating CVD risk associated with low, median, and high values of HDL-P subclass 1 ("H1") as a function of increasing levels of an inflammatory biomarker (as shown, GlycA) (predicted probabilities for CVD events in MESA during a 9-year follow-up (n=458/5660) from logistic regression for a 60-year old non-smoking, non-diabetic Caucasian female with hypertension, BMI=29 kg/m2, LDL-P=1500 nmol/L, VLDL-P=130 nmol/L). Low, median, and high H1 values are 4.1, 5.7, and 7.2 μmol/L ($20^{th}$, $50^{th}$ and $80^{th}$ percentile), respectively, according to embodiments of the present invention.

FIG. 19 illustrates the significance of low, median, and high values of the small diameter HDL-P subclass ("H1") versus increasing levels of an inflammatory biomarker (as shown, GlycA) based on predicted probabilities for CVD events in MESA during a 9 year follow-up (n=458/5660) from logistic regression for a 60-year old non-smoking, non-diabetic Caucasian female with hypertension, BMI=29 kg/m², LDL-P=1500 n/mol/L, VLDL-P=130 mg/dL). Low, median, and high H1 values for this example, are 4.1, 5.7, and 7.2 μmol/L ($20^{th}$, $50^{th}$ and $80^{th}$ percentile), respectively, according to embodiments of the present invention. As shown, high values of H1 go from a lower CVD percent probability relative to low and median values at lower concentration ranges of the inflammatory biomarker but transition to the same risk at about 350 μmol/L GlycA. A high level of H1 is associated with increased CVD risk for GlycA above about 350 μmol/relative to the low and median concentrations of H1. Stated another way, a high H1 value is "good" (protective) when inflammation is low (<~350 μmol/L), but becomes "bad" (atherogenic) when systemic inflammation levels are higher (>350 μmol/L).

Figure 20:
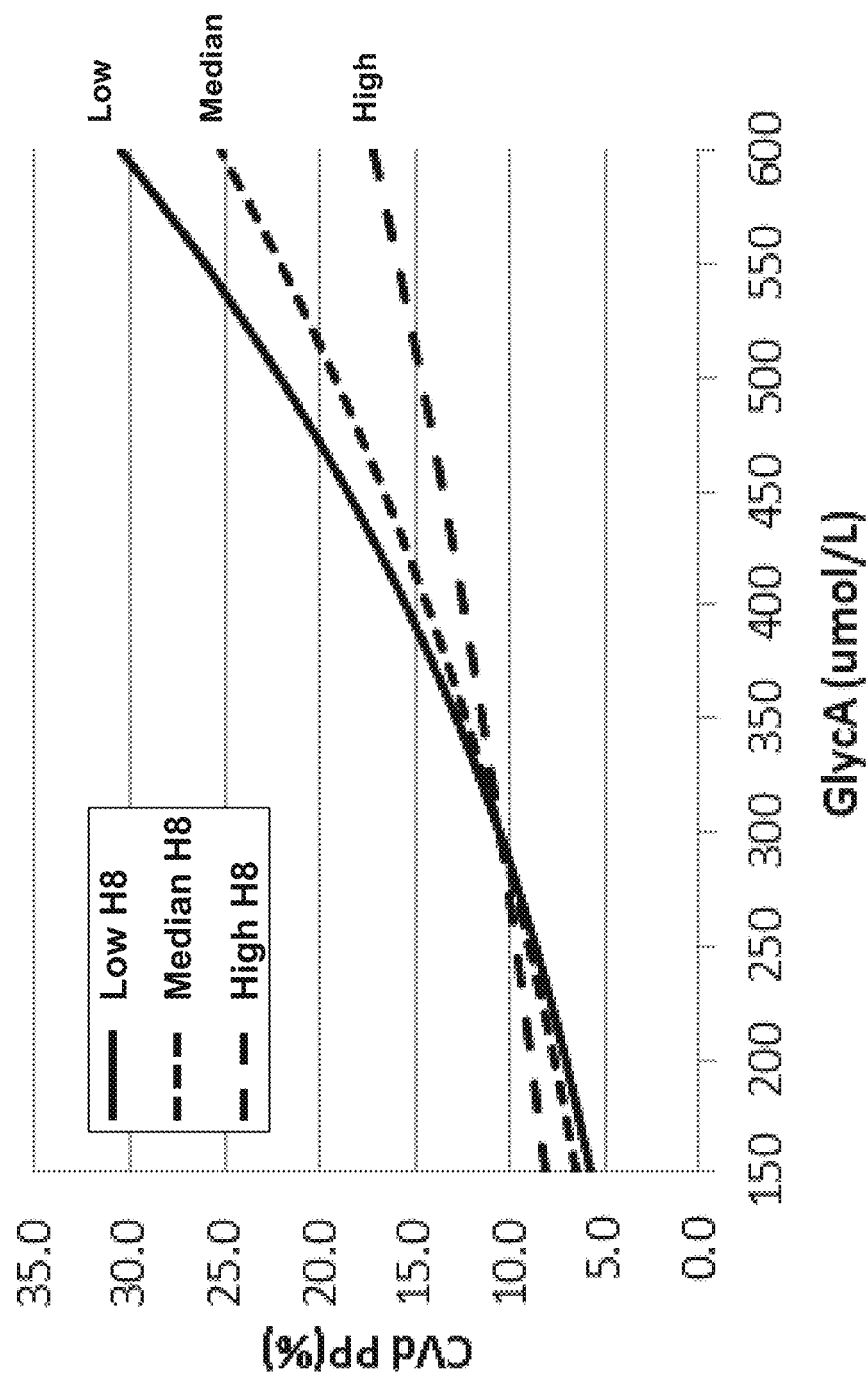
FIG. 20 is a graph illustrating CVD risk associated with low, median, and high values of HDL-P subclass 8 ("H8") as a function of increasing levels of an inflammatory biomarker (as shown, GlycA) (predicted probabilities for CVD events in MESA during a 9-year follow-up (n=458/5660) from logistic regression for a 60-year old non-smoking, non-diabetic Caucasian female with hypertension, BMI=29 kg/m2, LDL-P=1500 nmol/L, VLDL-P=130 nmol/L). Low, median, and high H1 values are 0.10, 0.27, and 0.59 μmol/L ($20^{th}$, $50^{th}$ and $80^{th}$ percentile), respectively, according to embodiments of the present invention.

FIG. 20 illustrates the significance of low, median, and high values of the large diameter HDL-P subclass ("H8") versus increasing levels of an inflammatory biomarker (as shown, GlycA) based on predicted probabilities for CVD events in MESA during a 9 year follow-up (n=458/5660) from logistic regression for a 60-year old non-smoking, non-diabetic Caucasian female with hypertension, BMI=29 kg/m², LDL-P=1500 n/mol/L, VLDL-P=130 mg/dL). Low, median, and high H8 values for this example, are 0.10, 0.27, and 0.59 μmol/L ($20^{th}$, $50^{th}$ and $80^{th}$ percentile), respectively, according to embodiments of the present invention. As shown, low values of H8 go from a marginally lower CVD percent probability relative to median and high H8 values at lower concentration ranges of the inflammatory biomarker but transition to the same risk at or just above about 300 μmol/L GlycA. Thus a low level of H8 is associated with increased CVD risk for GlycA above about 300 μmol/L relative to the median and high concentrations of H8.

D. A Gender-Specific Multimarker Improves CVD Prediction

Women generally have lower CVD risk than men. This phenomenon is not sufficiently explained by HDL cholesterol differences. Very surprisingly, analysis of the GlycA interaction with the small and large diameter HDL subclasses, H1 and H8, by gender revealed that their relations with CVD risk appear to be highly gender-specific. That is, H1 and its interaction with inflammation as assessed by GlycA are predictive of CVD events in men, while H8 and its GlycA interaction are specific to women's CVD events. Therefore, the development of gender-specific multimarkers based at least partially on H1 (for men) and H8 (for women) may be appropriate. A test or testing system that takes into account gender differences for CVD risk would be particularly desirable.

FIG. 21 is a chart that illustrates the combination of H8, GlycA, the H8*GlycA interaction parameter, and total HDL-P to generate $(HxI)^W$ for incident CVD events (n=171) in female MESA participants (n=2901) according to some particular embodiments of the present invention. When combined, the statistical relevance improves relative to the use of these parameters individually. The GlycA*H8 interaction parameter is shown by the Wald Chi-square ($\chi^2$) statistic to be associated with women's CVD risk at least as strongly as some other CVD risk factors, e.g., diabetes, BMI, LDL-P, VLDL-P, and HDL-P.

FIG. 22 is a chart that illustrates the combination of H1, GlycA, the H1*GlycA interaction term, and total HDL-P to generate $(HxI)^M$ for incident CVD events (n=287) in male MESA participants (n=2759) according to some particular embodiments of the present invention. When combined, the statistical relevance improves relative to the use of these parameters individually. The GlycA*H1 interaction parameter is shown by the Wald Chi-square ($\chi^2$) statistic to be associated with men's CVD risk at least as strongly as some other CVD risk factors, e.g., race, smoking, BMI, LDL-P, VLDL-P, and HDL-P.

Figure 23A:
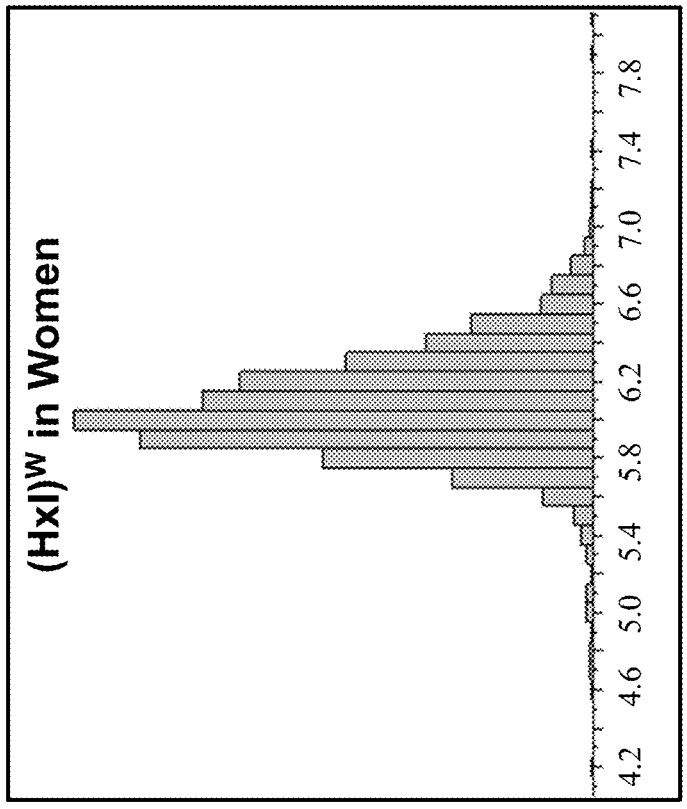
FIGS. 23A and 23B show a graph of distributions of $(HxI)^M$ values (unitless) in the MESA study population of men (n=2759) and a graph of distributions of $(HxI)^W$ values in the MESA study population of women (n=2901), respectively, based on embodiments of the present invention.
Figure 23B:
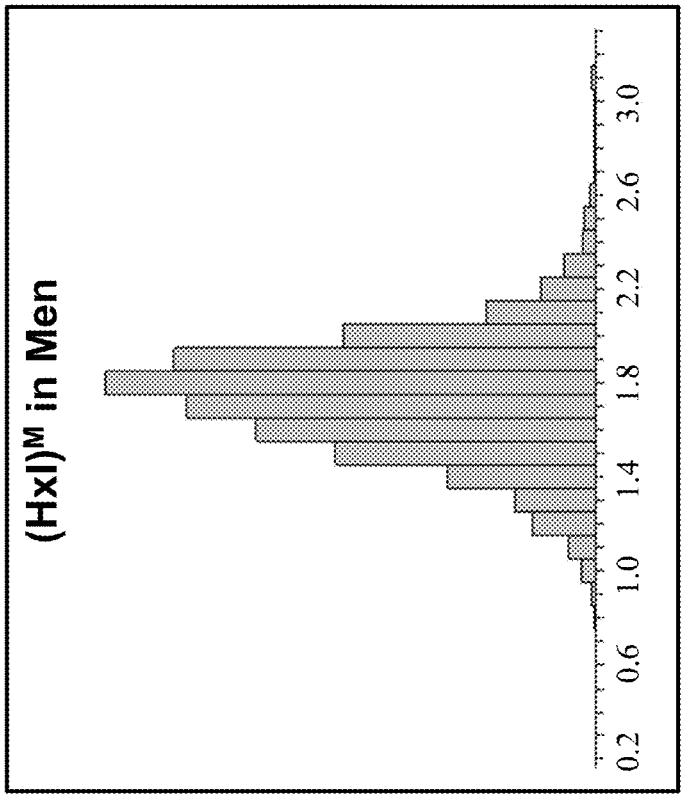

FIGS. 23A and 23B illustrate the distributions of the gender-specific multimarkers in MESA participants (male, n=2770 and female, n=2913), illustrating a bell-shaped distribution for each. Panel A shows distribution for $(HxI)^M$ and Panel B shows distribution for $(HxI)^W$. The men's multimarker shows bell-shaped distribution ranging between about 0.7564 and about 3.5430 with a mean of about 1.7408 and a standard deviation of about 0.2659. The women's multimarker shows bell-shaped distribution ranging between about 3.9493 and about 12.3421 with a mean of about 6.0693 and a standard deviation of about 0.3131. Notably, the distribution is normal or nearly normal, like cholesterol or other CVD biomarkers.

Figure 24:
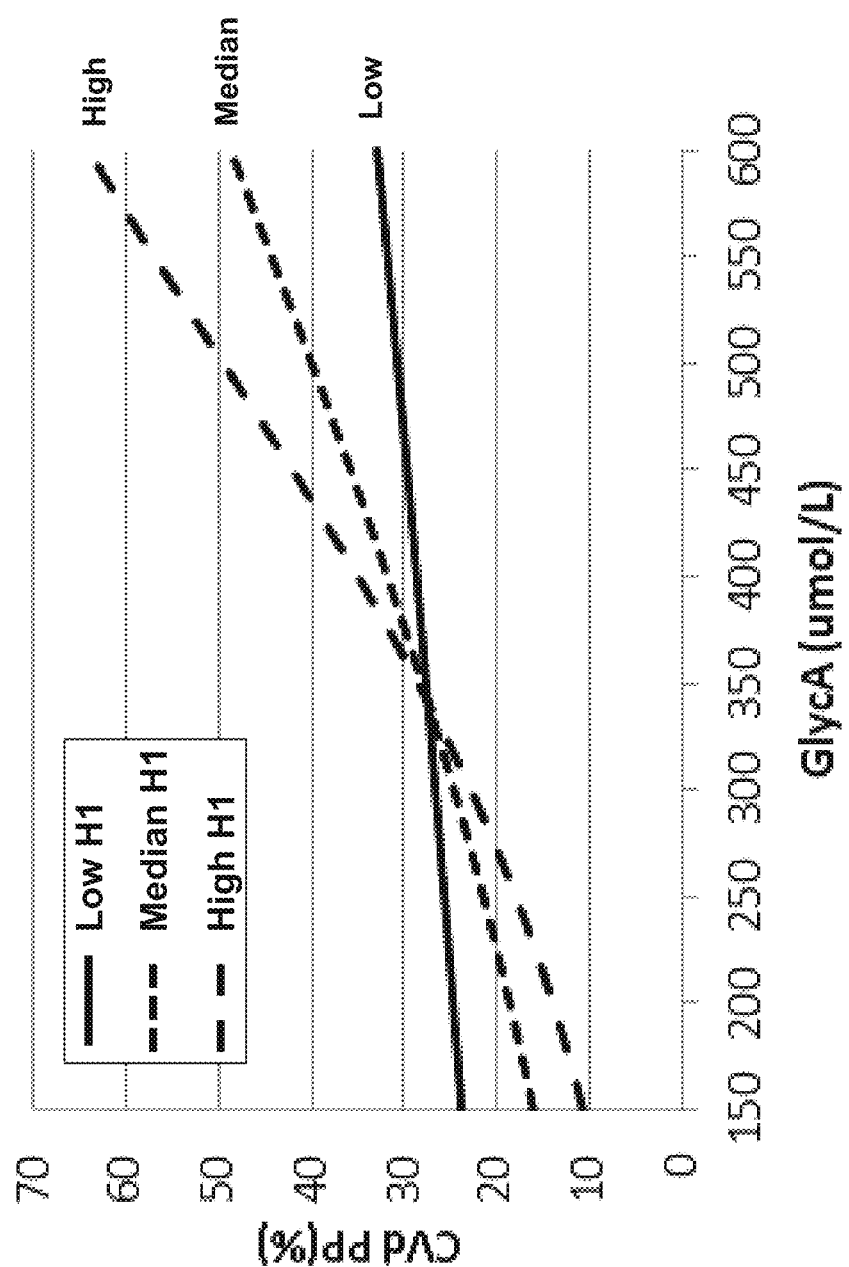
FIG. 24 is a graph illustrating CVD risk associated with low, median, and high values of HDL-P subclass 1 ("H1") in men as a function of increasing levels of an inflammatory biomarker (as shown, GlycA) (predicted probabilities for CVD events in MESA men during a 9-year follow-up (n=287/2759) from logistic regression for a 60-year old non-smoking, non-diabetic Caucasian male with hypertension, BMI=29 kg/m$^2$, LDL-P=1500 nmol/L, VLDL-P=130 nmol/L), and HDL-P=19.4 μmol/L. Low, median, and high H1 values are 4.7, 6.1, and 7.5 μmol/L ($20^{th}$, $50^{th}$ and $80^{th}$ percentile), respectively, according to embodiments of the present invention.

FIG. 24 illustrates the significance of low, median and high values of H1 versus increasing levels of inflammatory biomarker GlycA, based on predicted probabilities for CVD events in MESA men during a 9 year follow-up (n=287/2759) for a 60-year old non-smoking, non-diabetic Caucasian man with hypertension, BMI=29 kg/m$^2$, LDL-P=1500 n/mol/L, VLDL-P=130 mg/dL, and HDL-P=19.4 μmol/L). Probabilities are based on coefficients from a logistic regression model of CVD events in MESA men for a male-specific multimarker $(HxI)^M$ that includes a H1*GlycA interaction term. Low, median, and high H1 values for this example, are 4.7, 6.1, and 7.5 μmol/L ($20^{th}$, $50^{th}$ and $80^{th}$ percentile), respectively, according to embodiments of the present invention. As shown, high values of H1 go from a lower CVD percent probability relative to low and median H1 values at lower concentration ranges of the inflammatory biomarker but transition to the same risk at about 350 μmol/L. A high level of H1 is associated with drastically increased CVD risk for GlycA above about 350 μmol/L relative to the low and median concentrations of H1. Thus the meaning of the H1 value (level) depends on inflammatory state. Increased inflammation with high levels of H1 is more atherogenic.

Figure 25:
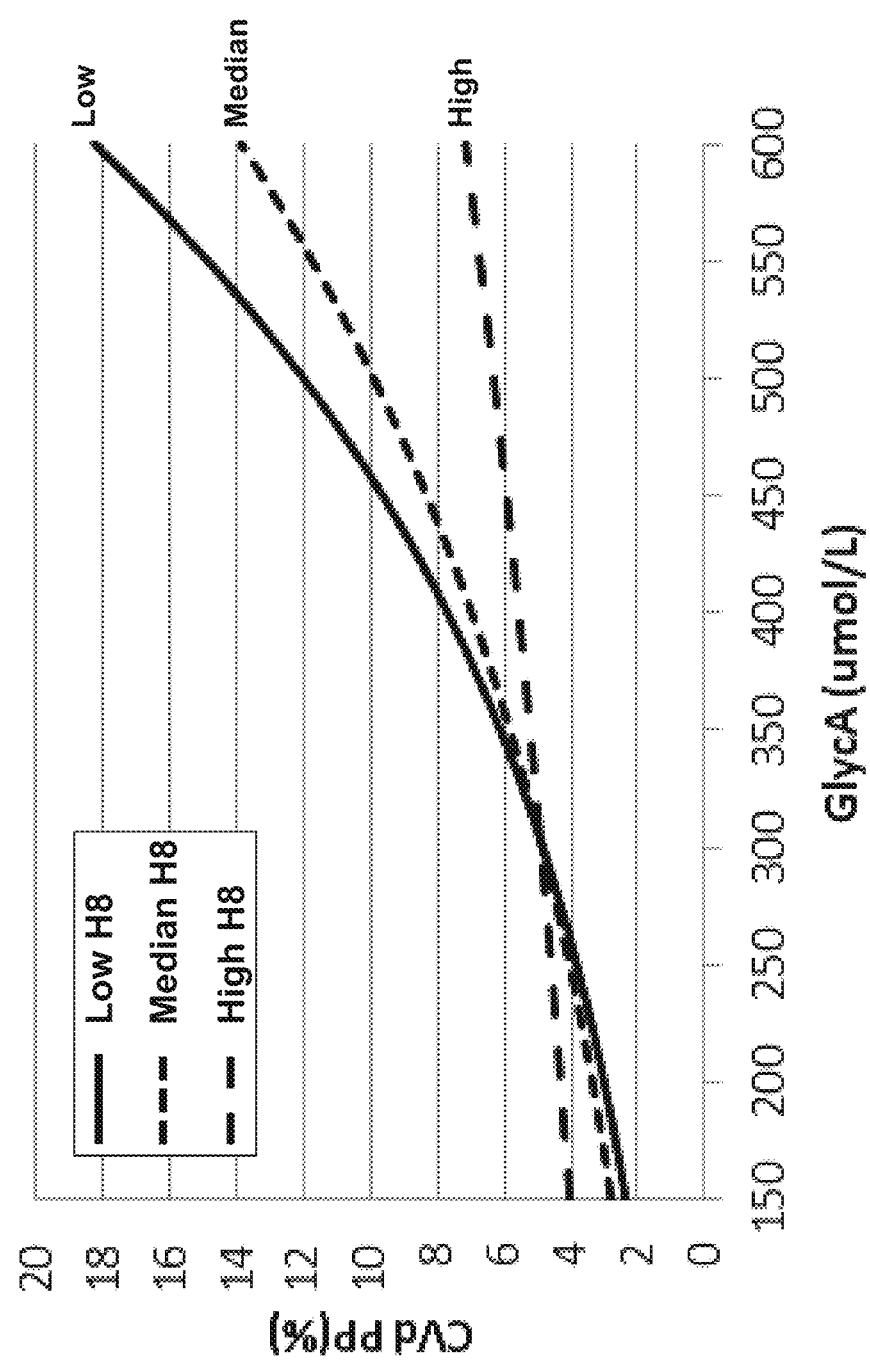
FIG. 25 is a graph illustrating CVD risk associated with low, median, and high values of HDL-P subclass 8 ("H8") in women as a function of increasing levels of an inflammatory biomarker (as shown, GlycA) (predicted probabilities for CVD events in MESA women during a 9-year follow-up (n=171/2901) from logistic regression for a 60-year old non-smoking, non-diabetic Caucasian female with hypertension, BMI=29 kg/m$^2$, LDL-P=1500 nmol/L, VLDL- P=130 nmol/L), and HDL-P=22.0 µmol/L. Low, median, and high H8 values are 0.12, 0.32, and 0.77 µmol/L ($20^{th}$, $50^{th}$ and $80^{th}$ percentile), respectively, according to embodiments of the present invention.

FIG. 25 illustrates the significance of low, median and high values of H8 versus increasing levels of inflammatory biomarker GlycA, based on predicted probabilities for CVD events in MESA women during a 9 year follow-up (n=171/2901) from logistic regression for a 60-year old non-smoking, non-diabetic Caucasian woman with hypertension, BMI=29 kg/m$^2$, LDL-P=1500 n/mol/L, VLDL-P=130 mg/dL, and HDL-P=22.0 μmol/L). Probabilities are based on coefficients from a logistic regression model of CVD events in MESA women for a female-specific multimarker $(HxI)^W$ that includes a H8*GlycA interaction term. Low, median and high H8 values for this example, are 0.12, 0.32, and 0.77 μmol/L ($20^{th}$, $50^{th}$ and $80^{th}$ percentile), respectively, according to embodiments of the present invention. As shown, low values of H8 go from a lower CVD percent probability relative to median and high H8 values at lower concentration ranges of the inflammatory biomarker but transition to the same risk at or just above about 300 μmol/L. A low level of H8 is associated with markedly increased CVD risk for GlycA above about 300 μmol/L relative to the median and high concentrations of H8. Thus the significance of the H8 value (level) also depends on inflammatory state. Increased inflammation with low levels of H8 is more atherogenic. As shown by the curves in the graph, the risk of someone with low H8 is hypersensitive to the GlycA level, compared to having higher H8 (i.e., the slope of the risk curve as a function of GlycA is much greater for low H8).

FIG. 26 shows model $\chi^2$ values for eight different prediction models which differ according to which variables are added to the "base" logistic regression model for incident CVD events in MESA women (n=169/2868), which includes age, sex/gender, race, hypertension, smoking, diabetes, BMI and VLDL-P. The increase in model $\chi^2$ when using $(HxI)^W$ in model 7 is about 13 points above "standard" or conventional risk assessments using LDL-C and HDL-C (model 2). This corresponds to improved prediction (i.e., improved risk evaluation) for women in model 7, for example.

FIG. 27 shows model $\chi^2$ values for eight different prediction models which differ according to which variables are added to the "base" logistic regression model for incident CVD events in MESA men (n=282/2722), which includes age, sex/gender, race, hypertension, smoking, diabetes, BMI and VLDL-P. The increase in model $\chi^2$ when using $(HxI)^M$ in model 7 is about 16 points above "standard" or conventional risk assessments using LDL-C and HDL-C (model 2). This corresponds to improved prediction (i.e., improved risk evaluation) for men in model 7, for example.

FIG. 28 shows the contributions of multimarkers $(HxI)^W$ and $(HxI)^M$ to CVD risk prediction in women and men as compared to traditional risk factors. The data are calculated from proportional hazards regression models for incident CVD events in MESA women (169 events/2868 subjects) and men (282 events/2722 subjects), respectively. Higher $\chi^2$ values indicate greater contribution from the given parameter to CVD risk prediction. For women, the gender-specific multimarker is second only to age as a predictive parameter. For men, only age and hypertension are more predictive. For both genders, the respective gender-specific multimarker is a stronger contributor than smoking, diabetes, or BMI.

Thus it appears that H1 is likely responsible for the HMSPxGlycA interaction observed in the deconvolution model having 26 HDL subclasses, and H8 is likely responsible for the observed HLPxGlycA interaction. The "genderless" $(HxI)^{CVD}$ multimarker was weakened by inclusion of the 2 component multimarkers (H1 & H8), one of which was irrelevant to the risk of men (H8) and the other of which was irrelevant to women (H1). The gender-specific multimarkers such as $(HxI)^W$ and $(HxI)^M$ may be employed to achieve better risk prediction for women and men by applying risk prediction parameters that are specific to gender.

E. Systems

Embodiments of the invention include methods, circuits, NMR spectrometers or NMR analyzers, non-transitory computer readable media, online semi-automated risk calculators, and processors that evaluate a person's CVD risk using measurements of defined parameters collected from an in vitro blood plasma or serum patient sample using a defined multi-component risk prediction model that includes at least one HDL and inflammatory biomarker interaction parameter.

FIGS. 29A and 29B illustrate that embodiments of the invention can provide an online risk calculator 100 (accessible to clinicians or patients/people on the internet) that can be accessible via the internet and presented on a display 100d of a computer, smartphone, electronic notebook and the like. The risk calculator 100 can include fields that can be automatically populated by measurements and/or with fields that allow a user to input associated parameters such as $(HxI)_{CVD}$, systolic blood pressure ("BP"), gender and age, for example, similar to the risk calculators currently provided by Framingham and the American Academy of Cardiologists, for example. The risk calculator 100 can provide a CVD risk output 100R.

Figure 30:
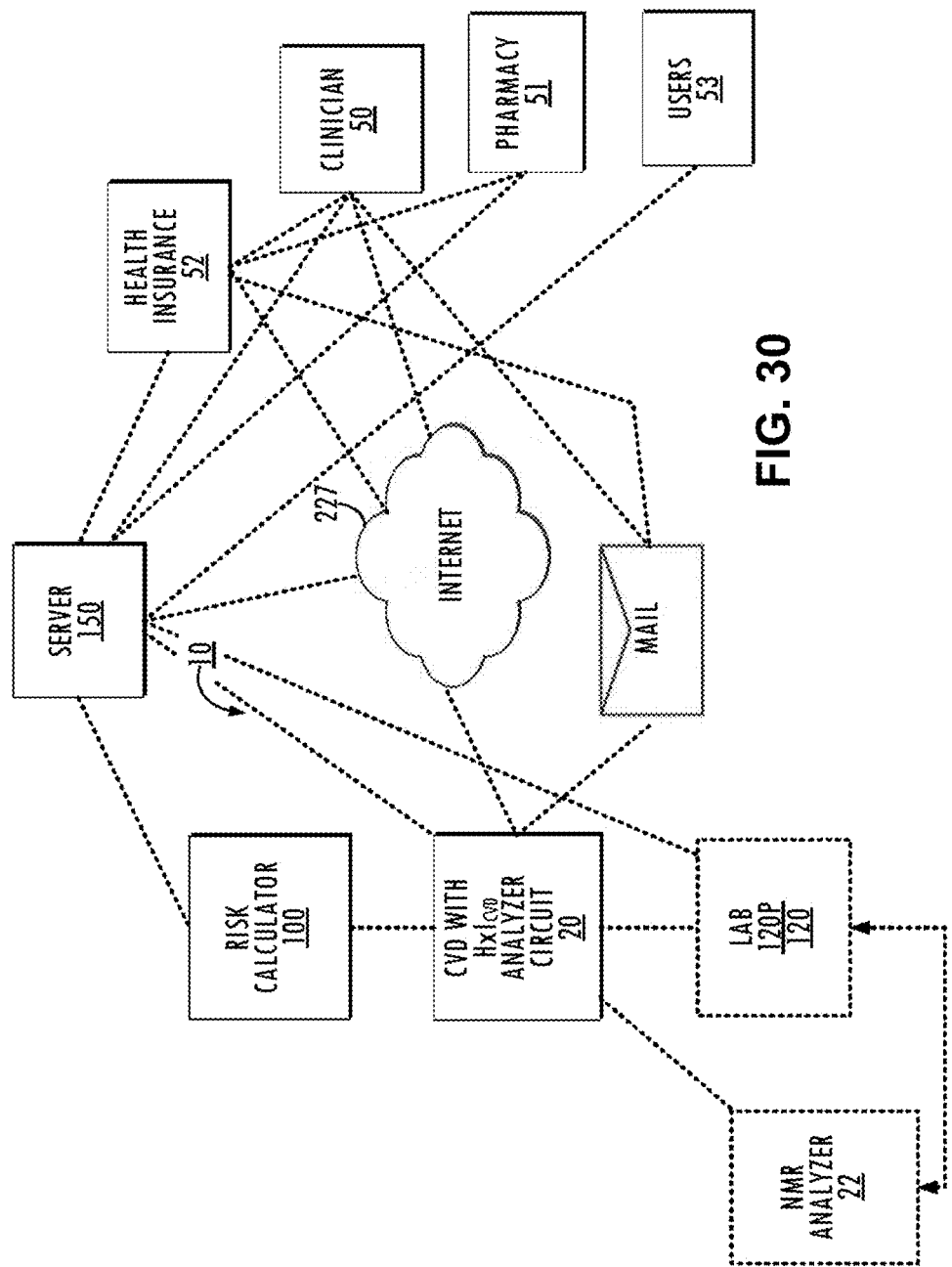
FIG. 30 is a schematic illustration of a system for analyzing a patient's CVD risk using a $(HxI)_{CVD}$ risk parameter module and/or circuit using according to embodiments of the present invention.

Referring now to FIG. 30, it is contemplated that the CVD risk analysis can be carried out using a system 10 in communication with a clinical laboratory 120 that evaluates biosamples to generate clinical measurements of at least one inflammatory biomarker and/or lipoproteins for measurements of (subclasses) of HDL-P and/or LDL-P, for example. The system 10 can include a CVD analysis circuit 20 that calculates the $(HxI)_{CVD}$ risk parameter. The analysis module or circuit 20 can reside totally or partially on one or more servers 150. The module or circuit 20 can be on-board a processor 120p at a respective laboratory 120 or remote from a processor at the laboratory and accessible via the server 150. The processor 120p can be held on a server or other electronic communications device, typically that complies with HIPAA requirements. The processor 120p can form part of an electronic medical records system or any electronic communication protocol at a laboratory (e.g., a LIS system).

Figure 34:
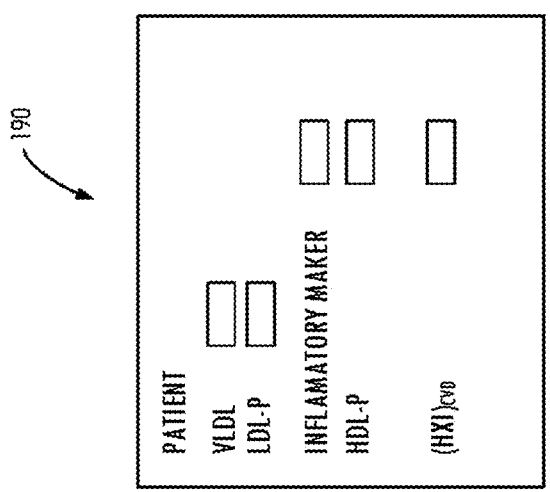
FIG. 34 is an example of a patient report that includes CVD risk evaluation comprising $(HxI)_{CVD}$ according to embodiments of the present invention.
Figure 35:
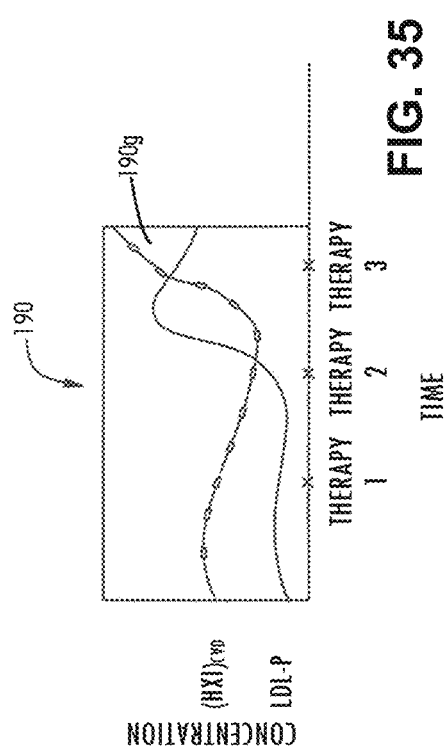
FIG. 35 is a prophetic example of a graph of $(HxI)_{CVD}$ values versus time that can be used to monitor change to evaluate a patient's risk status, change in status, and/or clinical efficacy of a therapy or even used for clinical trials or to contradict planned therapies and the like according to embodiments of the present invention.

In some embodiments, the laboratory 120 includes an NMR analyzer 22 that is configured to generate all or some of the measurements for the $(HxI)_{CVD}$ risk parameter. The analysis module or circuit 20 can reside totally or partially on the NMR analyzer 22, partially or totally in the processor 120p and the analyzer 22, totally or partially in the server 150, or distributed between the analyzer 22, various processors and/or servers. The NMR analyzer 22 can be in communication with the processor 120p which may be local or remote to the laboratory 120. The processor 120p may perform deconvolution of an NMR signal or spectrum obtained from a biosample analysis. The circuit 20 can collect inputs from various sources for measurements of the inputs used to calculate the CVD risk and/or the $(HxI)_{CVD}$ risk parameter. For example, the inflammatory marker measurement may be provided by one laboratory or machine in the laboratory and the lipoprotein measurements by another laboratory or machine in the same laboratory and the measurements can be transmitted to the circuit 20 for calculation of the $(HxI)_{CVD}$ risk parameter. The circuit 20 can also be configured to generate a patient report 190 (FIGS. 34, 35). FIG. 35 illustrates the report 190 can include a graph 190g of the $(HxI)_{CVD}$ risk parameter over time for a patient report (FIG. 35) which may allow for better therapy decisions.

The server 150 can be provided using cloud computing which includes the provision of computational resources on demand via a computer network. The resources can be embodied as various infrastructure services (e.g. compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Data transfer can be encrypted and can be done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and test data.

The results of the analysis can be transmitted via a computer network, such as the Internet, via email or the like to a clinician site 50, to a health insurance agency 52 or a pharmacy 51 or other user 53. The results can be sent directly from the analysis site or may be sent indirectly. The results may be printed out and sent via conventional mail. This information can also be transmitted to pharmacies and/or medical insurance companies, or even patients that monitor for prescriptions or drug use that may result in an increased risk of an adverse event. The results can be sent to a patient via email to a "home" computer or to a pervasive computing device such as a smart phone or notepad and the like. The results can be as an email attachment of the overall report or as a text message alert, for example. Users can access the information using an internet portal to access the online risk calculator.

Figure 31:
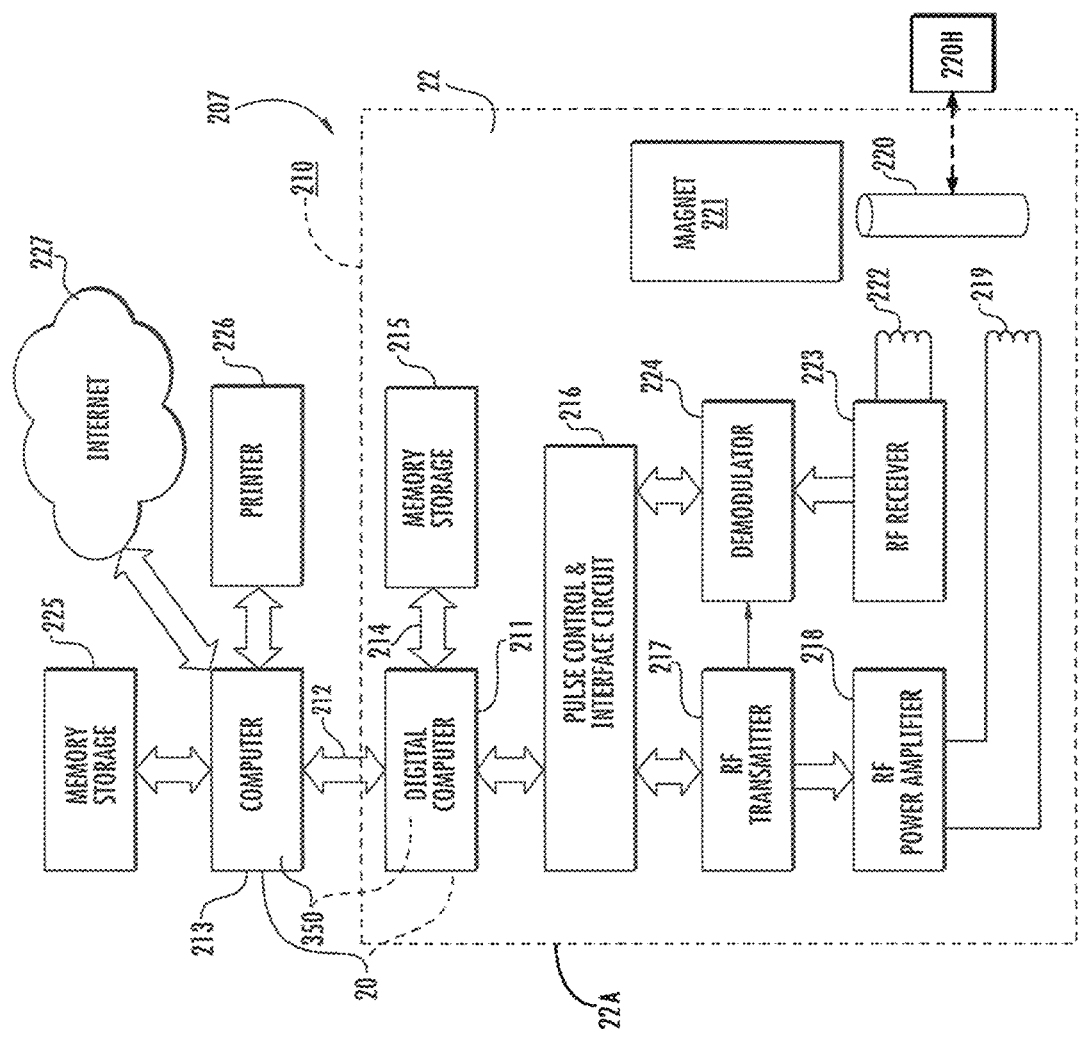
FIG. 31 is a schematic illustration of a NMR spectroscopy apparatus according to embodiments of the present invention.

Referring now to FIG. 31, a system 207 with an NMR analyzer 22A for acquiring and calculating the lineshape of biosamples is illustrated. Further details of an exemplary NMR analyzer 22A are described in U.S. Pat. No. 8,013,602, the contents of which are hereby incorporated by reference as if recited in full herein.

The system 207 includes an NMR spectrometer 22 for taking NMR measurements of a sample and a sample handler 20H, which is typically an interactive sample handler that allows for flow NMR, although containers may also be used to hold the samples in the bore of the spectrometer. In one embodiment, the spectrometer 22 is configured so that the NMR measurements are conducted at 400 MHz for proton signals; in other embodiments the measurements may be carried out at 360 MHz or other suitable frequency. Other frequencies corresponding to a desired operational magnetic field strength may also be employed, typically between about 200 MHz-900 MHz. Typically, a proton flow probe is installed, as is a temperature controller to maintain the sample temperature at 47+/−0.5 degrees C. The spectrometer 22 is controlled by a digital computer 214 or other signal processing unit. The computer 211 should be capable of performing rapid Fourier transformations. It may also include a data link 212 to another processor or computer 213, and a direct-memory-access channel 214 which can connects to a hard memory storage unit 215. A processor or computer 213 may deconvolve an NMR spectrum.

The digital computer 211 may also include a set of analog-to-digital converters, digital-to-analog converters and slow device I/O ports which connect through a pulse control and interface circuit 216 to the operating elements of the spectrometer. These elements include an RF transmitter 217 which produces an RF excitation pulse of the duration, frequency and magnitude directed by the digital computer 211, and an RF power amplifier 218 which amplifies the pulse and couples it to the RF transmit coil 219 that surrounds sample cell 220. The NMR signal produced by the excited sample in the presence of a 9.4 Tesla polarizing magnetic field produced by superconducting magnet 221 is received by a coil 222 and applied to an RF receiver 223. The amplified and filtered NMR signal is demodulated at 224 and the resulting quadrature signals are applied to the interface circuit 216 where they are digitized and input through the digital computer 211. The lipoprotein measurements, inflammatory biomarker measurement and $(HxI)_{CVD}$ analyzer circuit 20 or module 350 (FIG. 32) can be located in one or more processors associated with the digital computer 211 and/or in a secondary computer 213 or other computers that may be on-site or remote, accessible via a worldwide network such as the Internet 227.

After the NMR data are acquired from the sample in the measurement cell 220, processing by the computer 211 produces another file that can, as desired, be stored in the storage 215. This second file is a digital representation of the chemical shift spectrum and it is subsequently read out to the computer 213 for storage in its storage 225 or a database associated with one or more servers. Under the direction of a program stored in its memory, the computer 213, which may be a personal, laptop, desktop, workstation, electronic notepad, smartphone or other computer, processes the chemical shift spectrum in accordance with the teachings of the present invention to generate a report which may be output to a printer 226 or electronically stored and relayed to a desired email address or URL. Those skilled in this art will recognize that other output devices, such as a computer display screen, notepad, smart phone and the like, may also be employed for the display of results.

It should be apparent to those skilled in the art that the functions performed by the computer 213 and its separate storage 225 may also be incorporated into the functions performed by the spectrometer's digital computer 211. In such case, the printer 226 may be connected directly to the digital computer 211. Other interfaces and output devices may also be employed, as are well-known to those skilled in this art.

Certain embodiments of the present invention are directed at providing methods, systems and/or computer program products that generate or employ $(HxI)_{CVD}$ risk parameter numbers that may be particularly useful in screening and/or risk assessment evaluations for CVD of in vitro biosamples.

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user=s computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

Figure 32:
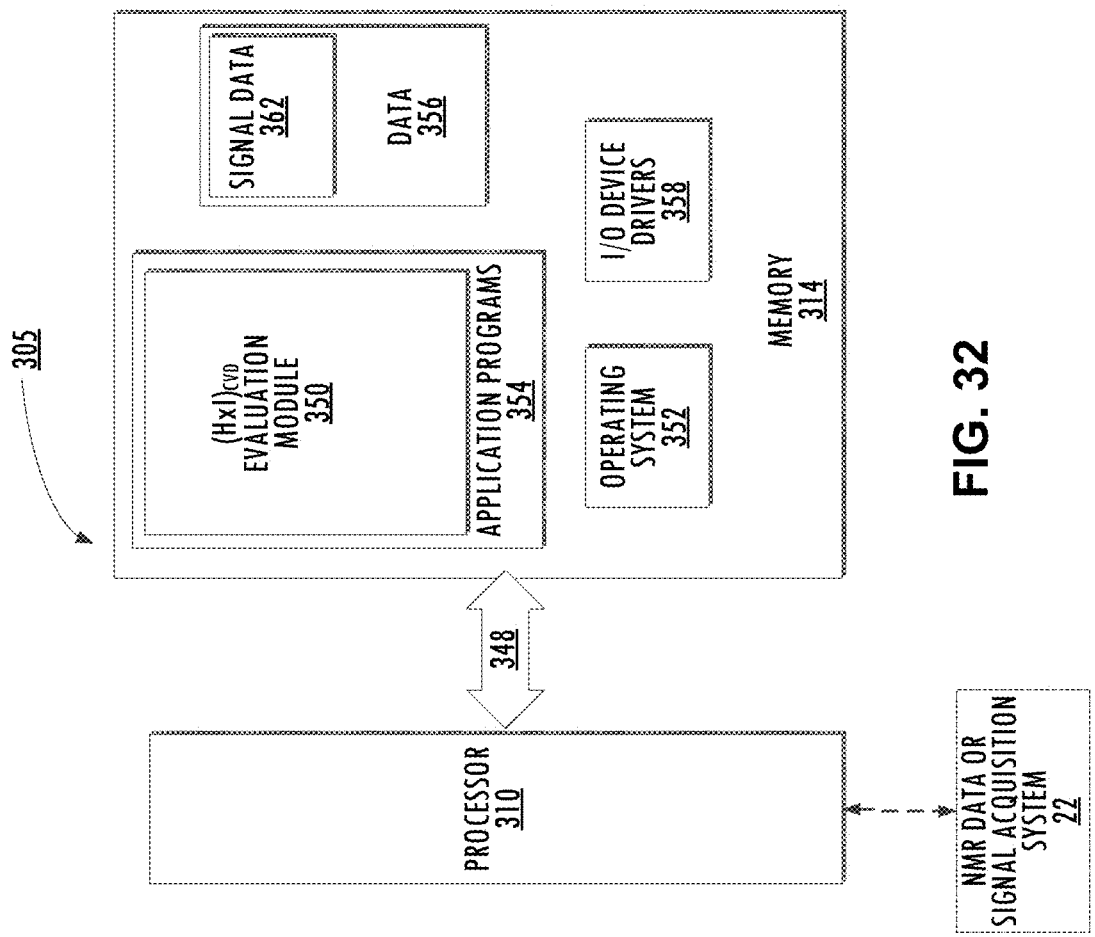
FIG. 32 is a schematic diagram of a data processing system according to embodiments of the present invention.

FIG. 32 is a block diagram of exemplary embodiments of data processing systems that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 32, the memory 314 may include several categories of software and data used in the data processing system 305: the operating system 352; the application programs 354; the input/output (I/O) device drivers 358; a $(HxI)_{CVD}$ risk parameter calculation Module 350; and the data 356. The Module 350 can sum concentrations of defined subpopulations of HDL, mathematically multiple the inflammatory biomarker concentration to one or more HDL-P parameter, apply the statistical coefficients and calculate a composite $(HxI)_{CVD}$ risk parameter.

The data 356 may include signal (constituent and/or composite spectrum lineshape) data 362 which may be obtained from a data or signal acquisition system 320. As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000 or WindowsXP from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Module 350 being an application program in FIG. 32, as will be appreciated by those of skill in the art, other configurations may also be utilized while still benefiting from the teachings of the present invention. For example, the Module 350 may also be incorporated into the operating system 352, the I/O device drivers 358 or other such logical division of the data processing system 305. Thus, the present invention should not be construed as limited to the configuration of FIG. 32, which is intended to encompass any configuration capable of carrying out the operations described herein.

In certain embodiments, the Module 350 includes computer program code for providing a measure of LDL-P and the $(HxI)_{CVD}$ risk parameter, which may include a series of the measurements taken over time, which may be used to indicate whether therapy intervention is desired and/or track efficacy of a therapy. It is contemplated that the $(HxI)_{CVD}$ risk parameter can be used for at least two different therapy decisions, such as increasing protective HDL-P and lowering inflammation to reduce CVD risk.

Figure 33:
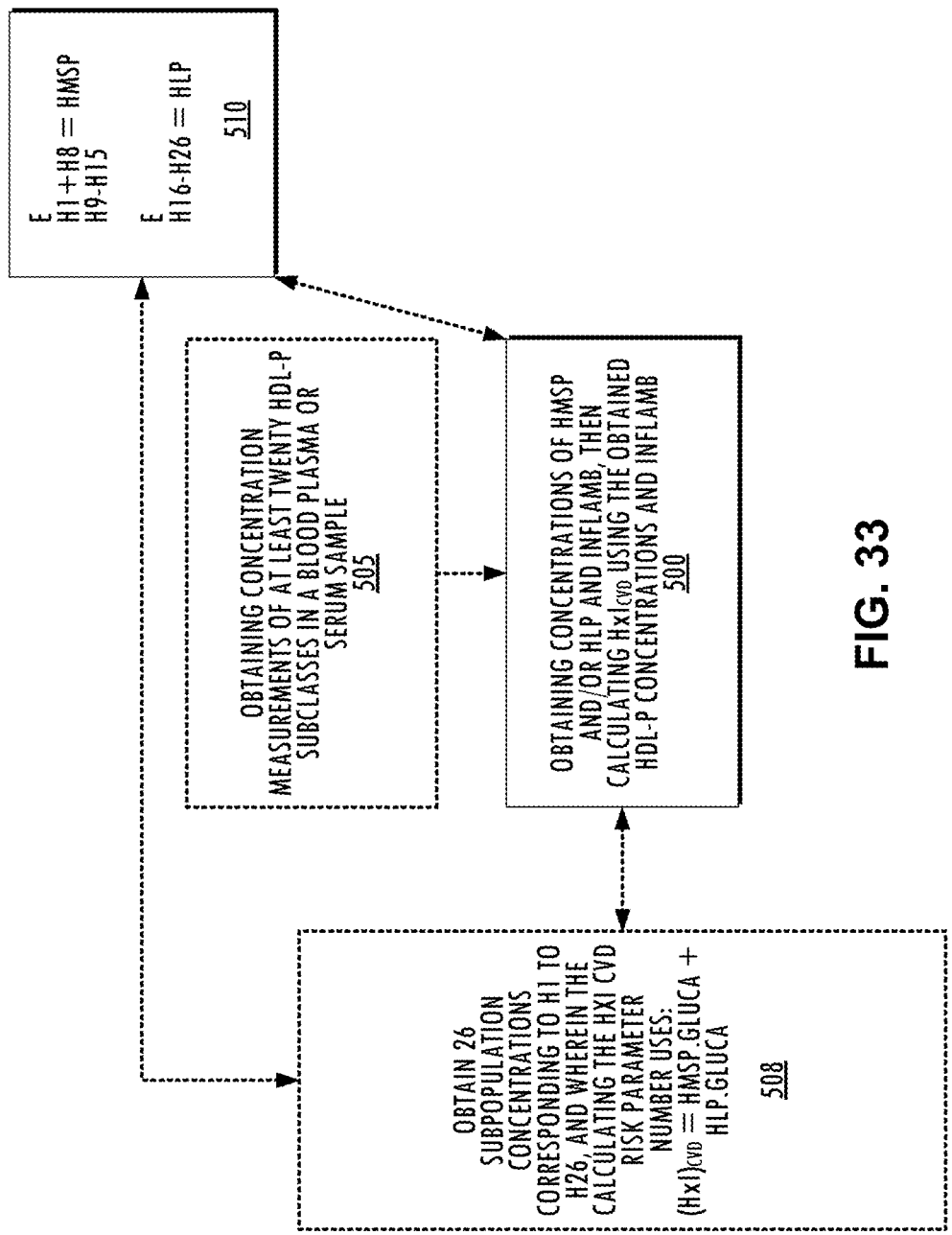
FIG. 33 is a flow chart of exemplary operations that can be used to assess CVD risk according to embodiments of the present invention.

FIG. 33 is a flow chart of exemplary operations that can be used to carry out embodiments of the invention for determining $(HxI)_{CVD}$ risk parameter numbers. Regarding the examples with analysis with 26 subpopulations of HDL-P, concentration measurements of small and medium HDL-P subclasses can be obtained and summed and/or concentrations of large HDL-P subclasses can be obtained. Concentration of at least one inflammatory biomarker (INFLAMB) can be obtained. At least one HDL and inflammatory interaction parameter can be calculated (INTERA or INTERB). An $(HxI)_{CVD}$ risk parameter can be generated using the at least one HDL and inflammatory interaction parameter (block 500). In some embodiments, measurements of at least twenty subpopulations of HDL-P subclasses in a blood plasma or serum sample can be obtained for the HDL-P concentration measurements (block 505). In some embodiments 26 subpopulation concentrations H1-H26 of HDL-P subclasses are obtained and the $(HxI)_{CVD}$ risk parameter calculation is carried out using two interaction parameters, which may optionally include: cHMSP*GlycA+ HLP*GlycA, using the obtained HDL-P and inflammatory biomarker concentration measurements (block 508). FIG. 33 demonstrates an example with 26 subpopulations, but the system can readily be adapted for 8 subpopulations of HDL-P or other subclassifications. The relevant subpopulation concentrations can be summed to generate total concentrations for subgroups of interest (block 510).

FIG. 34 is a schematic illustration of an exemplary patient test report 190 that can include various lipoprotein parameters such as LDL-P, VLDL and the $(HxI)_{CVD}$ risk parameter. The protective HDL-P number can be presented with a risk assessment data correlated to population norms, typical ranges, and/or degree of risk.

FIG. 35 illustrates that a graph 190g of the $(HxI)_{CVD}$ risk parameter can be provided to illustrate a change in patient metabolic HDL function over time due to age, medical intervention or a therapy according to some embodiments. Tracking this parameter may provide better clinical indicators of efficacy of a therapy and/or a better risk predictor for CHD for patients.

As shown in FIG. 35, the $(HxI)_{CVD}$ risk parameter can be used to monitor a patient over time to correlate known start or use of a drug or other therapy to evaluate whether HDL function has been altered and/or whether CVD risk has increased or decreased using such therapy.

Future drugs or uses of known drugs can be identified, screened or tested in patients identified using the $(HxI)_{CVD}$ risk parameter.

Thus, in some embodiments, the invention comprises a system for determining a risk parameter for cardiovascular disease or events, comprising a component for obtaining measurements of HDL particles and at least one inflammatory biomarker in a biosample from a subject; a component for determining concentrations for at least one individual HDL particle size subclass and the at least one inflammatory biomarker, based on the measurements; and a component for programmatically calculating a risk parameter $((HxI)_{CVD})$ of the subject using at least the concentrations for the at least one subclass of HDL particle and the at least one inflammatory biomarker.

In some embodiments, the component for obtaining measurements comprises an NMR analyzer. In some embodiments, the system further comprises a component that deconvolves a composite NMR spectrum of a fitting region of a plasma sample of a subject using a defined deconvolution model with at least eight HDL-P subclasses. In some embodiments, the component for determining and/or calculating comprises at least one processor.

In some embodiments, the component for determining is configured to determine concentrations for HDL-P subclasses cH1-cH8. In some embodiments, the component for determining is configured to determine concentrations for at least one of (i) cH1 having a diameter in the range of 7.0-7.6 nm; or (ii) cH8 having a diameter in the range of 11.5-13.5 nm.

In some embodiments, the system is configured to calculate an $(HxI)_{CVD}$ risk parameter and/or monitor the $(HxI)_{CVD}$ risk parameter as a therapeutic target for either (a) raising or lowering HDL-P values or (b) lowering inflammation, or both (a) and (b). In some embodiments, the system is configured to calculate a measurement of GlycA multiplied by a concentration of a defined subpopulation of high density lipoprotein particles (HDL-P).

In some embodiments, the components for obtaining measurements and determining concentrations comprise an NMR spectrometer for acquiring at least one NMR spectrum of an in vitro blood plasma or serum sample; and a processor in communication with the NMR spectrometer, the processor configured to (i) obtain concentration measurements of at least eight subpopulations of high density lipoprotein particle (HDL-P) subclasses in a blood plasma or serum sample, and (ii) calculate a $(HxI)_{CVD}$ risk parameter using a defined subset of the obtained HDL-P concentration measurements, and at least one interaction parameter comprising the product of a concentration of at least one defined HDL-P subclass with a concentration of at least one inflammation biomarker.

In some embodiments, the inflammatory biomarker comprises GlycA, wherein the at least one interaction parameter includes one interaction parameter defined by GlycA concentration multiplied by at least one HDL-P subclass concentration, wherein the at least one HDL-P subclass demonstrates gender specificity for CVD events in a study population for the associated risk parameter.

Embodiments of the invention can be used to evaluate a patient's risk of having or developing cardiovascular disease using one or more interaction parameters. Embodiments of the invention provide a new biomarker, the $(HxI)_{CVD}$ risk parameter which may be monitored independent of the overall risk as a therapy target. In some embodiments, the risk is for a 2-10 year time frame and/or a 5-10 year time frame, using a plurality of defined risk model parameters. However, the risk model may be based on other time frames.

Thus in some embodiments, the present invention comprises methods of evaluating a subject's cardiovascular risk, or assessing a therapy and/or drug, comprising: obtaining measurements of HDL particles and at least one inflammatory biomarker in a biosample from the subject; determining concentrations for at least one individual HDL particle size subclass and the at least one inflammatory biomarker, based on the measurements; and programmatically calculating a risk parameter $((HxI)_{CVD})$ of a subject using at least one interaction parameter comprising concentrations for the at least one subclass of HDL particle and the at least one inflammatory biomarker.

In other embodiments, the invention comprises methods, circuits, NMR spectrometers or NMR analyzers, online semi-automated risk calculators and processors that evaluate a person's CVD risk using measurements of defined parameters from an in vitro blood plasma or serum patient sample using a defined multi-component risk progression model that includes at least one HDL and at least one inflammatory biomarker interaction parameter.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A computer program product for determining a risk parameter for cardiovascular disease or events according to the method of:

using a Nuclear Magnetic Resonance spectrometer to obtain measurements of HDL particles and inflammatory biomarker GlycA on a biosample from a subject;

determining NMR-derived concentrations for at least one individual HDL particle size subclass and the inflammatory biomarker GlycA, based on the measurements;

programmatically calculating a risk parameter $((HxI)_{CVD})$ of the subject using at least the concentrations for the at least one individual HDL particle size subclass and the inflammatory biomarker GlycA; and determining a subject's risk of having and/or developing CVD based, at least in part, on the $(HxI)_{CVD}$ risk parameter number.

2. A computer program product for determining a risk parameter for cardiovascular disease or events, the computer program product comprising:

a non-transitory computer readable storage medium having computer readable program code embodied in the medium, the computer readable program code comprising:

computer readable program code that obtains concentration measurements from a Nuclear Magnetic Resonance spectrometer for at least eight subclasses of HDL-P in a blood plasma or serum sample and for inflammatory biomarker GlycA; and computer readable program code that calculates a risk parameter $((HxI)_{CVD})$ comprising at least one interaction parameter defined by the concentration of GlycA multiplied by the concentration of one or more of the at least eight subclasses of HDL-P.

3. The computer program product of claim 2, wherein the non-transitory computer readable storage medium further comprises computer readable program code for deconvolving a composite NMR spectrum of a fitting region of a plasma sample of a subject, wherein the computer readable program code deconvolves the composite NMR spectrum using a defined deconvolution model with the at least eight HDL-P subclasses.

4. The computer program product of claim 2, wherein the non-transitory computer readable storage medium further comprises computer readable program code that determines concentrations for HDL particle size subclasses cH1-cH8.

5. The computer program product of claim 2, wherein the non-transitory computer readable storage medium further comprises computer readable program code for determining concentrations for at least one of the following individual HDL particle sizes:
(i) cH1 having a diameter in the range of 7.0-7.6 nm; or
(ii) cH8 having a diameter in the range of 11.5-13.5 nm.

6. The computer program product of claim 2, wherein the non-transitory computer readable storage medium further comprises computer readable program code for calculating $(HxI)_{CVD}$ according to one of the following equations:

$$(HxI)_{CVD} = c_1(cH1) + c_2(INFLAM) + c_3(INTER_{H1}); \text{ or}$$

$$(HxI)_{CVD} = c_4(cH8) + c_5(INFLAM) + c_6(INTER_{H8})$$

wherein INFLAM is the concentration of the inflammatory biomarker GlycA, $INTER_{H1} = INFLAM*cH1$, $INTER_{H8} = INFLAM*cH8$, and wherein "$c_1$-$c_6$" represent coefficients from a mathematical model of CVD events in a study population for the associated risk parameter.

7. The computer program product of claim 2, wherein the non-transitory computer readable storage medium further comprises computer readable program code for determining the concentration of an HDL-P subclass cH1, having an average diameter in the range of 7.0-7.6 nm to provide a male-specific HDL-inflammation multimarker.

8. The computer program product of claim 2, wherein the non-transitory computer readable storage medium further comprises computer readable program code for determining the concentration of an HDL-P subclass cH8, having an average diameter in the range of 11.5-13.5 nm to provide a female-specific HDL-inflammation multimarker.

9. The computer program product of claim 2, wherein the non-transitory computer readable storage medium further comprises computer readable program code for electronically providing the calculated $(HxI)_{CVD}$ to a medical professional and/or patient report.

10. The computer program product of claim 2, wherein the non-transitory computer readable storage medium further comprises computer readable program code for prescribing or recommending a treatment for the subject based at least in part on the calculated $(HxI)_{CVD}$.

11. The computer program product of claim 2, wherein the non-transitory computer readable storage medium further comprises computer readable program code for programmatically calculating at least one interaction parameter defined by GlycA concentration multiplied by concentration for at least one of the HDL-P subclasses, wherein the at least one HDL-P subclass demonstrates gender specificity for CVD events in a study population for the associated risk parameter.

\* \* \* \* \*